United States Patent [19]
Alving et al.

[11] Patent Number: 5,753,260
[45] Date of Patent: May 19, 1998

[54] VACCINES AGAINST STEROLS

[75] Inventors: Carl R. Alving, Bethesda, Md.; Julie Kenner, Aiea, Hi.; Glenn M. Swartz, Jr., Jessup; John W. Madsen, Knoxville, both of Md.

[73] Assignee: EntreMed, Inc., Rockville, Md.

[21] Appl. No.: 422,633

[22] Filed: Apr. 14, 1995

Related U.S. Application Data

[63] Continuation of Ser. No. 164,109, Dec. 9, 1993, abandoned, which is a continuation-in-part of Ser. No. 997,954, Dec. 29, 1992, abandoned, which is a continuation-in-part of Ser. No. 624,957, Dec. 10, 1990, abandoned, which is a continuation-in-part of Ser. No. 601,090, Oct. 22, 1990, abandoned, and Ser. No. 444,214, Dec. 1, 1989, abandoned, which is a continuation-in-part of Ser. No. 875,048, Jun. 17, 1986, Pat. No. 4,885,256, said Ser. No. 601,090, is a continuation-in-part of Ser. No. 202,509, Jun. 2, 1988, abandoned.

[51] Int. Cl.$^6$ .............. A61K 9/27; A61K 39/00
[52] U.S. Cl. .............. 424/450; 424/184.1
[58] Field of Search .............. 424/184.1, 193.1, 424/450

[56] References Cited

U.S. PATENT DOCUMENTS

| | | | |
|---|---|---|---|
| 4,241,046 | 12/1980 | Papahadjopoulos et al. | 424/19 |
| 4,767,720 | 8/1988 | Lingwood | 436/536 |
| 4,885,256 | 12/1989 | Alving et al. | 436/578 |
| 4,952,569 | 8/1990 | Simons | 424/88 |
| 5,026,557 | 6/1991 | Estis et al. | 424/450 |
| 5,100,662 | 3/1992 | Bolcsak et al. | 424/88 |

FOREIGN PATENT DOCUMENTS

| | | |
|---|---|---|
| A-0 356 340 | 2/1990 | European Pat. Off. |
| M-704M | 7/1961 | France . |
| A-50-088 219 | 7/1975 | Japan . |
| WO-A-9206709 | 4/1992 | WIPO . |

OTHER PUBLICATIONS van Dalen et al (1988) J. Controlled Release 1:123–132.

New, R.R.C., et al., "Antileishmanial acitivity of amphotericin and other antifungal agents entrapped in liposomes," *Journal of Antimicrobial Chemotherapy*, vol. 8, pp. 371–381 (1981).

Taylor, R.L., et al., "Amphotericin B in Liposomes: A Novel Therapy for Histoplasmosis," *Am. Rev. Respir. Dis.*, vol. 125, pp. 610–611 (1982).

Graybill, J.R. et al., "Treatment of Murine Cryptococcosis with Liposome–Associated Amphotericin B," *The Journal of Infectious Diseases*, vol. 145, No. 5, pp. 748–752 (May 1982).

Lopez–Berestein, G. et al., "Effects of Sterols on the Therapeutic Efficacy of Liposomal Amphotericin B in Murine Candidiasis," *Cancer Drug Delivery*, vol. 1, No. 1, pp. 37–42 (1983).

(List continued on next page.)

*Primary Examiner*—Ponnathapura Achutamurthy
*Attorney, Agent, or Firm*—Jones & Askew

[57] ABSTRACT

The present invention relates to immunoreactive compositions and methods for immunizing humans or animals against sterols, such as cholesterol and its derivatives, and their use in methods for reducing the serum cholesterol levels of the immunized individuals and to retard or reduce the severity of atherosclerosis or atherosclerosis plaques caused by ingestion of dietary cholesterol. Another embodiment of the present invention encompasses ergosterol or ergosterol derivative compositions useful for the treatment or prevention of fungal infection, and methods of use thereof. Yet another aspect of the invention is dairy products containing anti-ergosterol antibodies produced by dairy animals immunized against ergosterol according to the present invention and methods of making thereof. A further aspect of the invention is a diagnostic assay for determining whether a human or animal has a fungal infection.

19 Claims, 6 Drawing Sheets

TIME COURSE OF IgG RESPONSE AGAINST PHOSPHATIDYLCHOLESTEROL

TIME FOLLOWING PRIMARY IMMUNIZATION (DAYS)

OTHER PUBLICATIONS

Ahrens, J. et al., "Treatment of Experimental Murine Candidiasis with Liposome–associated Amphotericin B," *Sabouraudia: Journal of Medical and Veterinary Mycology*, vol. 22, pp. 163–166 (1984).

Hopfer, R.L. et al., "In Vitro Antifungal Activities of Amphotericin B and Liposome–Encapsulated Amphotericin B," *Antimicrobial Agents and Chemotherapy*, vol. 25, No. 3, pp. 387–389 (Mar. 1984).

Mehta, R. et al., "Liposomal Amphotericin B Is Toxic To Fungal Cells But Not To Mammalian Cells," *Biochimica et Biophysica Acta*, vol. 77, pp. 230–234 (1984).

Juliano, R. et al., "Pharmacokinetic and Therapeutic Consequences of Liposomal Drug Delivery: Fluorodeoxyuridine and Amphotericin B as Examples," *Biology of the Cell*, vol. 47 pp. 39–46 (1983).

Berger, E. et al., "On the Specificity of Antibodies to Substances from the Lipoid Class," *Z. Immunitaet*, vol. 76 pp. 16–35 (1932).

Wadsworth, A. et al., "The Antigenic Action of Cholesterol," *Journal of Immunobiology*, vol. 29, pp. 135–149 (1935).

Wiseman, H. et al., "Mechanism of Inhibition of Lipid peroxidation by Tamoxifen and 4–hydroxytamoxifen Introduced to Liposomes," *FEBS Letters*, vol. 274, No. 1,2, pp. 107–110 (Nov. 1990).

Alving, C.R. et al., "Antibodies to Cholesterol, Cholesterol Conjugates, and Liposomes: Implications for Atherosclerosis and Autoimmunity," *Critical Reviews in Immunology*, vol. 10, Issue 5, pp. 441–453 (1991).

Franek, Milan, "Structural Aspects of Steroid–Antibody Specificity," *Journal of Steroid Biochemistry*, vol. 28, No. 1, pp. 95–108 (1987).

Fantl, V.E et al., "Production and Characterization of a Monoclonal Antibody to Progesterone," *Journal of Steroid Biochemistry*, vol. 14, pp. 405–107 (1981).

Fantl, V.E. et al., "Characterization of Monoclonal Antibodies Raised Against Testosterone," *Journal of Steroid Biochemistry*, vol. 19, No. 5, pp. 1605–1610 (1983).

Fantl, V.E. et al., "Simultaneous Production of Monoclonal Antibodies to Dehydroepiandrosterone, Ostradiol Progesterone and Testosterone," *Journal of Endrocrinology*, vol. 100, pp. 367–376 (1984).

Brochu, M. et al., "Monoclonal Antibodies for Use with Iodine–Labeled Radioligands in Progesterone Radioimmunoassay," *Journal of Steroid Biochemistry*, vol. 21, No. 4 pp. 405–411 (1984).

Klopstock, A. et al., "Antibodies Reacting with Steroid Haptens," *Journal of Immunology*, vol. 92, pp. 515–519 (1964).

Swartz, Jr., G.M. et al., "Antibodies to Cholesterol," *Proc. National Academy of Sciences*, vol. 85, pp. 1902–1906 (Mar. 1988).

Alving, C.R. et al., "Naturally Occurring Autoantibodies to Cholesterol in Humans," *Biochemical Transactions, 629th Meeting, London*, vol. 17, pp. 637–639 (1989).

Gerlier, D. et al., "Liposomes as a Tool to Study the Role of Membrane Presentation in the Immunogenicity of a MuL V–Related Tumor Antigen," *The Journal of Immunology*, vol. 131, No. 1, pp. 485–490 (Jul. 1983).

Bangham, A.D. et al., "Diffusion of Univalent Ions Across the Lamellae of Swollen Phospholipids," *Journal of Molecular Biology*, vol. 13, pp. 238–252 (1965).

Bruckdorfer, K.R. et al., "The Incorporation of Steroid Molecules into Lecithin Sols, β–Lipoproteins and Cellular Membranes," *European Journal of Biochemistry*, vol. 4, pp. 512–518 (1968).

Bruckdorder, K.R. et al., "The Effect of Partial Replacements of Membrane Cholesterol by Other Steroids on the Osmotic Fragility and Glycerol Permeability of Erythrocytes," *Bichimica et Biophysica Acta*, vol. 183, pp. 334–335 (1969).

Banerji, B. et al., "Antibodies to Liposomal Phosphatidylserine and Phosphatidic Acid," *Biochemical Cell Biology*, vol. 68, pp. 96–100 (1990).

Alving, C. et al., "Cholesterol–Dependent Human Complement Activation Resulting In Damage To Liposomal Model Membrane," *The Journal of Immunology*, vol. 118, No. 1, pp. 342–347 (Jan., 1977).

Bailey, J.M. et al., "Immunization with a Synthetic Cholesterol–ester Antigen and Induced Atherosclerosis in Rabbits," *Nature*, vol. 201, No. 4917, pp. 407–408 (Jan. 25, 1964).

Brown, M.S. et al., "A Receptor–Mediated Pathway for Cholesterol Homeostatis," *Science*, vol. 232, pp. 34–47 (Apr. 4, 1986).

Sato, J. et al., "Anti–cholesterol Activity in Antisera Against Human Serum Lipoprotiens," *Immunochemistry*, vol. 9, No. 5, pp. 585–587 (May, 1972).

Banerji, B. et al., "Membrane Lipid Composition Modulates the Binding Specificity of a Monoclonal Antibody Against Liposomes," *Biochimia et Biophysica Acta*, vol. 689, pp. 319–326 (1982).

Rook, G., "Immunity to Viruses, Bacteria and Fungi," *Immunology*, The C.V. Mosby Company, St. Louis, pp. 16.14–16.15 (1989).

Playfair, J.H.L., "Vaccines: Still Needed," *Immune Intervention*, Academic Press, London, pp. 1–12 (1984).

Fries, L.F., et al., "Liposomal Malaria Vaccine in Humans: A Safe and Potent Adjuvant Strategy," *Proc. National Academy of Sciences*, vol. 89, pp. 358–362 (Jan. 1992).

Langer, R., "New Methods of Drug Delivery," *Science*, vol. 249, pp. 1527–1533 (Sep. 28, 1990).

Alving, C.R., et al., "Adjuvanticity of Lipid A and Lipid A Fractions in Liposomes," *Liposome and Immunobiology*, Elsevier North Holland, Inc., New York, pp. 67–78 (1980).

Klimov et al., "Cholesterol Metabolism in Rabbits with Resistance to Experimental Atherosclerosis Aquired by Immunological Treatment," *Vopr. Med. Khim.*, vol. 6, pp. 803–807 (1977) (abstract in English).

Sato et al., "Anticholeseremic antibody," *Chemical Abstracts*, vol. 83, No. 18, abstract No. 152332m (1975).

Alving et al., "Liposomes as vehicles for vaccines," *Prog. Clin. Biol. Res.*, vol. 47, pp. 339–355 (1980).

Goodman, D.S. et al., "Report of the National Cholesterol Education Program Expert Panel on Detection, Evaluation and Treatment of High Blood Cholesterol in Adults," *Arch. Intern, Med.*, vol. 148, pp. 36–69 (1988).

Kromhout, D. et al., "Serum cholesterol and 25–year incidence of and mortality from myocardial infraction and cancer," *Arch Intern, Med.*, vol. 148, pp. 1051–1055 (1988).

Luepker, R.V. et al., "Recommendations regarding public screening for measuring blood cholesterol. Summary of a National Heart, Lung and Blood Institute Workshop (Oct. 1988)," *Arch. Intern. Med.*, vol. 149, pp. 2650–2654 (1989).

Alving, "Antibodies to liposomes, phospholipids and cholesterol: Implications for autoimmunity, atherosclerosis and aging," *Horizons in Membrane Biotechnology*, Nicolau, C. and Chapman, D. eds., Wiley–Liss, pp. 40–41 (1990).

Alving et al., "Preparation and Use of Liposomes in Immunological Studies," *Liposome Technology 2nd. Ed., Vol. III: Interactions of Liposomes with the Biological Milieu*, Gregoridis ed., CRC Press, Boca Raton, pp. 317–343 (1993).

Hara et al., "Immunological Properties of Phosphatidycholesterol and its Homologue,"*Chemistry and Physics of Lipids*, vol. 23, pp. 7–12 (1979).

Collins et al., "The Stability and Structure of Cholesterol-–rich Codispersions of Cholesterol and Phosphatidylcholine," *J. Lipid Res.*, vol. 23, pp. 291–298 (1982).

Ahmad et al., "Liposomal Amphoterician–B in the control of experimental aspergillosis in mice: Part I—Relative therapeutic efficacy of free and liposomal Amphotericin–B," *Indian Journal of Biochemistry & Biophysics*, vol. 26, pp. 351–356 (1989).

Sevier et al., "Monoclonal Antibodies in Clinical Immunology," *Clinical Chem.*, vol. 27, pp. 1797–1806 (1981).

Kobayashi et al., "Production and specificity of antisera raised against 25–hydroxyvitamin D3–[C–3]–bovine serum albumin conjugates," *Steroids*, vol. 57, pp. 488–493 (1992).

Zalc, B. et al., "Immunogenic Properties of Glucosylceramide," *Molecular Immunology*, vol. 16, pp. 297–300 (1979).

Alving, "Antibodies to Liposomes, Phospholipids and Phosphate Esters," Chemistry and Physics of Lipids, vol. 40, pp. 303–314 (1986).

Wassef, N.M. et al., "Phosphate Binding Specificities of Monoclonal Antibodies Against Phosphoinsitides in Liposomes," *Molecular Immunology*, vol. 21, No. 10, pp. 863–868 (1984).

Alving, C.R. et al., "Preparation and Use of Liposomes in Immunological Studies," *Liposome Technology*, vol. 2, CRC Press, Boca Raton, pp. 157–175 (1984).

Fig_1
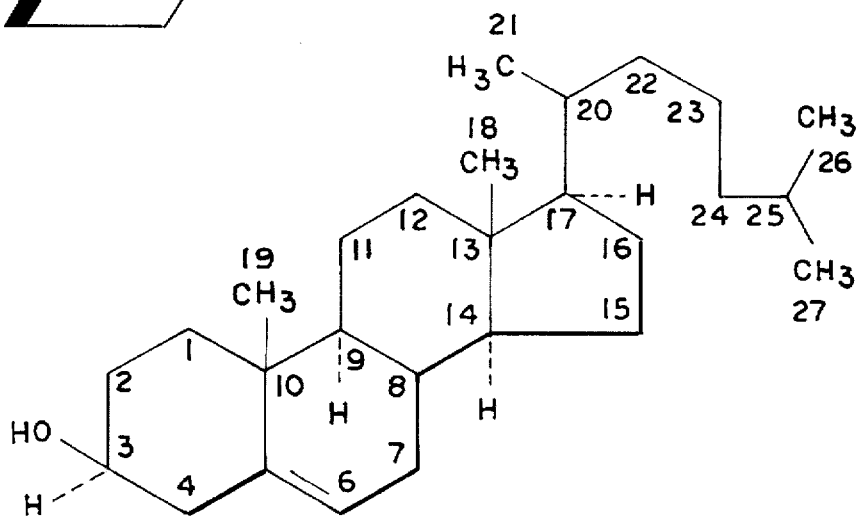
CHOLESTEROL
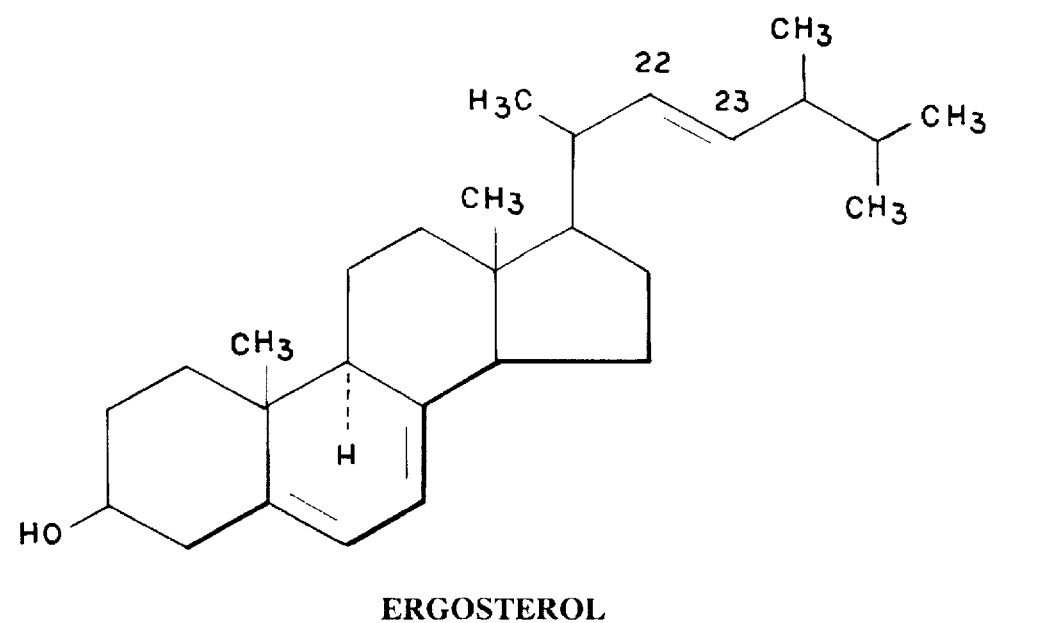
ERGOSTEROL
Fig_2

PHOSPHATIDYLCHOLESTEROL (17B-LINKAGE)

PHOSPHATIDYLCHOLESTEROL (3B-LINKAGE)

CHOLESTEROL ESTER

PHOSPHATIDYLCHOLESTEROL

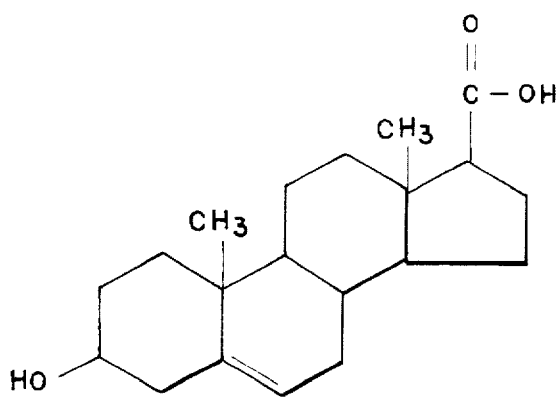
5-ANDROSTEN-3B-OL-17B-CARBOXYLIC ACID
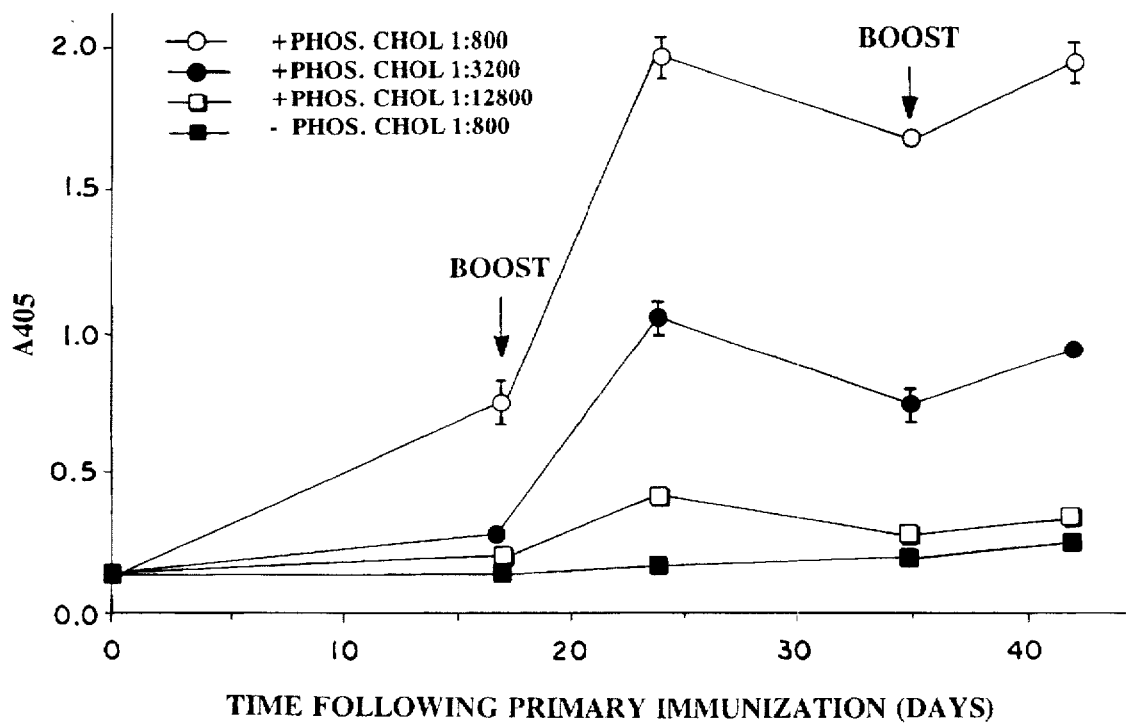

Fig. 8

IgG REACTIVITY OF ANTISERA AGAINST INDIVIDUAL LIPOSOMAL COMPONENTS

ELISA TITER VERSUS ANTIGEN:

| MICE INOCULATED WITH: | PHOS CHOL | CHOL | CHOL OLEATE | CHOL MYRISTATE | 4-CHOLESTEN-3-ONE | ERGOCAL-CIFEROL | LIPID A | DMPC | DMPG |
|---|---|---|---|---|---|---|---|---|---|
| 43% CHOL + 10% PHOSCHOL | 6400 | 400 | 200 | 200 | 200 | 800 | 3200 | 200 | 200 |
| 43% CHOL + 20% PHOSCHOL | 12800 | 800 | 200 | 200 | 200 | 800 | 3200 | 200 | 200 |
| 0% CHOL + 10% PHOSCHOL | 6400 | 400 | 200 | 200 | 200 | 1600 | 6400 | 200 | 200 |
| 43% CHOL + CHOL OLEATE | <200 | 400 | 200 | 200 | 200 | 200 | 6400 | 200 | 200 |
| 43% CHOL + CHOLMYNSTATE | <200 | 800 | 200 | 400 | 200 | 400 | 6400 | 200 | 200 |
| 43% CHOL + 4 CHOLESTEN-3-ONE | <200 | 400 | 200 | 200 | 200 | 400 | 3200 | 200 | 200 |
| 43% CHOL + ERGOCALCIFEROL | <200 | 400 | 200 | 200 | 200 | 400 | 3200 | 200 | 200 |
| 43% CHOL | <200 | 200 | 200 | 200 | 200 | 200 | 6400 | 200 | 200 |
| 71% CHOL | <200 | 400 | 200 | 200 | 200 | 400 | 6400 | 200 | 200 |
| NONE (PREBLEED) | <200 | <200 | <200 | <200 | <200 | <200 | <200 | <200 | <200 |

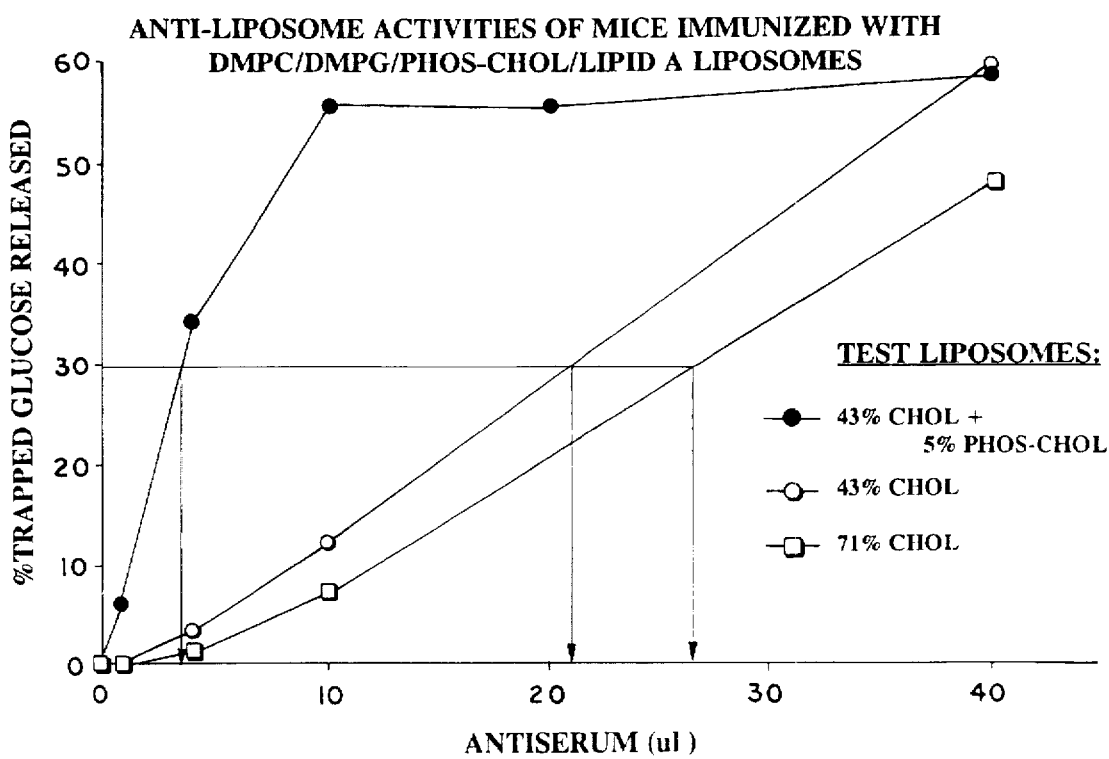
Fig_10
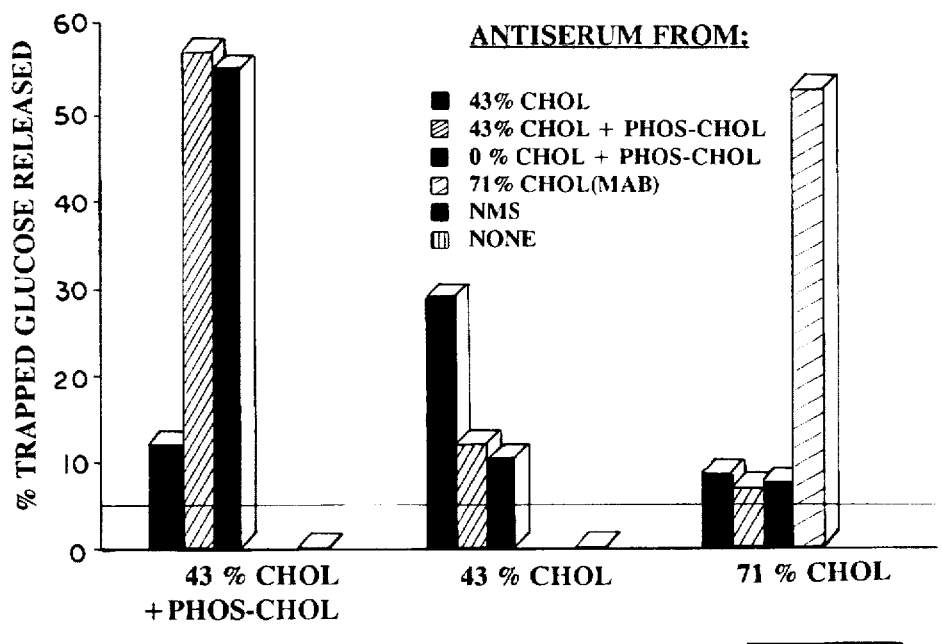
Fig_11

VACCINES AGAINST STEROLS

CROSS-REFERENCE TO RELATED APPLICATIONS

The present application is a continuation of U.S. patent application Ser. No. 08/164,109, filed Dec. 9, 1993, abandoned, which is a continuation-in-part of U.S. patent application Ser. No. 07/997,954, filed Dec. 29, 1992, abandoned, which is a continuation-in-part of U.S. patent application Ser. No. 07/624,957, filed Dec. 10, 1990, abandoned, which is a continuation-in-part of both U.S. patent application Ser. No. 07/601,090 filed Oct. 22, 1990, abandoned, itself a continuation-in-part of U.S. patent application Ser. No. 07/202,509 filed Jun. 2, 1988, abandoned, and U.S. patent application Ser. No. 07/444,214 filed Dec. 1, 1989, abandoned, itself a continuation-in-part of U.S. patent application Ser. No. 06/875,048 filed Jun. 17, 1986 which issued as U.S. Pat. No. 4,885,256.

GOVERNMENT INTEREST

The United States Government may have certain interests in the inventions described herein.

FIELD OF THE INVENTION

The present invention relates to immunoreactive compositions and methods for immunizing or hyperimmunizing humans or animals against sterols. More particularly, the present invention relates to vaccines against cholesterol and derivatives of cholesterol, and ergosterol and derivatives of ergosterol. The present invention is useful for reducing the serum cholesterol levels of an immunized human or animal and to retard or reduce the severity of atherosclerosis or atherosclerotic plaques caused by ingestion of dietary cholesterol or by other factors. Additionally, the invention relates to immunoreactive ergosterol or ergosterol derivative compositions and methods for administering the compositions to humans and animals for immunizing or hyperimmunizing humans and animals against fungal infections. The present invention also relates to anti-ergosterol antibody-containing dairy products. Also, the present invention relates to a diagnostic assay for determining whether a human or animal has a fungal infection.

BACKGROUND OF THE INVENTION

High levels of serum cholesterol are a significant causative effect in the pathogenesis of atherosclerosis and associated diseases such as atherosclerotic coronary heart disease, atherosclerotic cerebral vascular disease, renal disease, etc. It is also believed that lowering of blood cholesterol levels is associated with amelioration of atherosclerotic vascular diseases (Goodman, D. S. et al., Report of the National Cholesterol Education Program Expert Panel on Detection, Evaluation, and Treatment of High Blood Cholesterol in Adults. *Arch. Intern. Med.* 148:36–69, 1988; Kromhout, D. et al., Serum cholesterol and 25-year incidence of and mortality from myocardial infraction and cancer. (See The Zutphen Study. *Arch. Intern. Med.* 148:1051–1055, 1988.) In 1984, a National Institutes of Health consensus development conference panel recommended a framework of detection and treatment of hypercholesterolemia. Based on this study, the National Cholesterol Education Program has made the well-known recommendation to adults: "Know your cholesterol number" (Luepker, R. V. et al., Recommendations regarding public screening for measuring blood cholesterol. Summary of a National Heart, Lung, and Blood Institute Workshop, October 1988. *Arch. Intern. Med.* 149:2650–2654, 1989).

The conventional methods recommended for achieving reduced serum cholesterol levels are through reduction of dietary intake of cholesterol and other fats, and treatment of hypercholesterolemic individuals with drugs designed to lower blood cholesterol. The blood cholesterol levels are particularly associated with homeostatic mechanisms related to levels of plasma lipoproteins that serve as carriers of cholesterol. The so-called dangerous lipoproteins, from the standpoint of atherosclerotic risk, are the low density lipoproteins ("LDL"). The levels of LDL are regulated by the functional activities of LDL receptors on the surfaces of cells, particularly in the liver (see Brown, M. S. and Goldstein, J. L. A receptor-mediated pathway for cholesterol homeostasis. *Science* 232:34–47, 1986). Many of the strategies for using drugs to reduce blood cholesterol involve interference with the processing of cholesterol derived from LDL (Brown and Goldstein, 1986). The extent that cholesterol can be reduced by diet is limited by numerous factors, and the reduction of cholesterol by drugs is often associated with unwanted side effects. In any case, a variety of additional variables, such as genetic background, stress, and age, can influence cholesterol levels. Additional methods for reduction of cholesterol would be expected to have beneficial health effects, particularly in individuals who receive such treatment before significant progression of atherosclerotic disease has occurred.

To our knowledge, humans have never been actively immunized against cholesterol. The safety of active immunization against cholesterol, as well as the potential consequences relating to serum cholesterol levels or progression of atherosclerosis due to intake of dietary lipids, has not been established. It has been demonstrated that human sera usually do contain varying quantities of "naturally-occurring" antibodies to cholesterol, depending on the individual serum (See Alving et al., Naturally occurring autoantibodies to cholesterol in humans. *Biochem. Soc. Trans.* 17:637–639 (1989)). However, there has not been any correlation of such naturally-occurring antibodies with serum cholesterol levels or with atherosclerosis.

The possibility has been discussed that naturally-occurring antibodies to cholesterol might be a normal part of the aging process and might contribute to (rather than ameliorate) atherosclerosis (Alving, C. R. Antibodies to liposomes, phospholipids, and cholesterol: Implications for autoimmunity, atherosclerosis, and aging. In: *Horizons in Membrane Biotechnology*. Nicolau, C. and Chapman, D., editors, Wiley-Liss, pp. 40–41, 1990).

Although the inventors have not found any prior art teaching the immunization of humans with cholesterol, in the literature there has been one description of an attempt to ameliorate hypercholesterolemia and atherosclerosis in rabbits by immunological means. Bailey et al. immunized rabbits with an antigen consisting of cholesterol conjugated to bovine serum albumin (See Bailey et al., Immunization with a synthetic cholesterol-ester antigen and induced atherosclerosis in rabbits. *Nature* 201:407–408 (1964)). Bailey et al. stated that the "mean antibody titer measured by an interfacial precipitation technique was 1:7000", but there was no attempt to produce or to measure antibodies that had specificity against cholesterol. The assay antigen consisted of the original conjugate, not cholesterol either alone or as part of another conjugate. Nowhere did Bailey et al. teach that they had induced antibodies to cholesterol, and they did not teach that antibodies to cholesterol could have been produced or that such antibodies might have played a role in the lowering of serum cholesterol levels or amelioration of atherosclerosis.

Bailey et al. observed a reduced hypercholesterolemia and less aortic plaque formation in the immunized animals that were fed a cholesterol-rich diet. However, in the absence of further information the antibody titer could have been entirely directed against the bovine serum albumin component and the cholesterol-albumin conjugate might simply have lowered cholesterol through nonspecific mechanisms, such as by nonspecific adsorption of serum cholesterol by the albumin. This latter explanation could be supported by the fact that albumin has a considerable degree of hydrophobicity and can be used as a reagent to promote solubility of cholesterol in an aqueous medium such as serum. The disclosure by Bailey et al. is too insufficient to draw any immunological conclusion regarding the role, if any, that antibodies to cholesterol may have played in the experimental results. It is probably because of this that Bailey et al. did not teach any such role.

Yet another embodiment of the invention relates to prevention and treatment of fungal infections in humans and animals. Among individuals who have reduced immunological function, for example, in those who have AIDS, cancer, trauma due to accidents or surgery, debilitative metabolic illnesses such as diabetes mellitus, persons whose blood is exposed to environmental microbes such as individuals having indwelling intravenous tubes, and even in some elderly individuals, fungal infections of blood and tissues can result in serious, even life-threatening, situations. Mortality rates in cancer patients who develop systemic fungal infections is very high. In other cases, fungal or fungus-like infections, usually introduced into the lungs through the air, are commonplace among large numbers of persons due to environmental exposures. Examples of the latter types of infections include: coccidioidomycosis which is indigenous to the San Joaquin Valley in California, and areas around Flagstaff, Ariz.; histoplasmosis, which is commonplace in the Midwest. Other common types of fungus, or fungus-like infections that can cause severe disseminated disease in immunocompromised patients include blastomycosis, crytococcosis, candidiasis, and mycobacterial infections such as tuberculosis.

It has been observed that fungi are the most common cause of nonbacterial infection in patients with leukemia and lymphoma, with *Candida* species and *Aspergillus* being the most common fungal species in cancer patients. These two infections are estimated to have a combined mortality of 20% (Lopez-Berestein, G., Mehta, R., Hopfer, R., Mehta, K., Hersh, E. M., and Juliano, R., Cancer Drug Delivery, 1:37–42, 1983). Certain other organisms that have parasitic properties, such as leishmaniasis, can mimic many of the disease-causing properties, behaviors, and pathologies of fungal infections.

A characteristic commonly shared by organisms that cause all of the above diseases is the presence of ergosterol as the predominant or sole sterol in place of cholesterol. Cholesterol is the major sterol that is found in mammalian cells and tissues. Ergosterol serves many of the physiological membrane-associated functions in these organisms that are served by cholesterol in mammals. Alteration of concentrations of cholesterol and ergosterol in lipid bilayer domains of plasma membranes has enormous effects on fluidity and permeability of the membranes, and the presence of ergosterol is essential for viability of certain microorganisms just as the presence of cholesterol is vital for viability of mammalian cells. The enormous importance of ergosterol is illustrated by the fact that ergosterol rather than cholesterol is the predominant sterol compound found in most plants. Cholesterol is rarely found in any membranes other than those of mammals, and cholesterol and ergosterol are rarely found in any species of bacteria.

Further, it is known that mammals concentrate antibodies in milk, including colostrum (the first post-partem milk produced) as well as subsequently produced milk. During cheese manufacturing, the antibodies may be concentrated in the whey. It has been previously demonstrated that immunization of dairy cows with antigens such as enterotoxic Gram negative *E. coli* or their CFA-1, CFA-2 pili results in the production of high concentrations of antibodies against the intact organisms and/or their infectious pili. The oral ingestion of milk products obtained from inoculated dairy animals, including whey, whey, concentrates, and other dairy products has been shown to result in the passive immunization of the recipient animal. The antibodies successfully survive and transit the stomach acidity and act in the gastrointestinal system to opsonize the ingested antigen, resulting in an antibody-organism complex that is harmlessly excreted.

What is needed are methods and compositions which can be used to vaccinate a human or an animal against sterols such as cholesterol or ergosterol. By vaccinating a human or animal against cholesterol, blood concentrations of cholesterol can be safely and inexpensively reduced. By vaccinating a human or animal against ergosterol, the human or animal can better resist infection by fungi. Further, by vaccinating a dairy animal against ergosterol the milk produced by the dairy animal will contain a high concentration of anti-ergosterol antibodies. Consequently, the milk and other dairy products derived therefrom will be resistant to fungus and may be used to passively immunize humans or animals.

SUMMARY OF THE INVENTION

The present invention comprises sterol-containing vaccines and methods which are effective in immunizing humans against sterols such as cholesterol and ergosterol. In one embodiment, the present invention includes a vaccine formulation that can be used to immunize humans against cholesterol and its derivatives and thereby lower the concentration of serum cholesterol, either through the immunization procedure itself or in combination with other methods commonly used to lower cholesterol.

An example of a suitable formulation is liposomes containing phosphatidylcholine, cholesterol, and lipid A in molar ratios of approximately 2:5:0.02 (where the molarity of lipid A is based on the molarity of phosphate in native lipid A). This ratio is not critical, however, because other ratios can be successful in accomplishing the same result. Delivery vehicles other than liposomes would also be suitable, including microcapsules, microspheres, lipospheres, polymers, and slow release devices could serve instead of liposomes. An experiment in rabbits has demonstrated that an anti-cholesterol vaccine of the present invention ameliorates diet-induced elevations of serum cholesterol.

Another embodiment of the present invention relates to lowering the cholesterol content of food animals. The present invention can be used to vaccinate food animals against cholesterol thereby reducing the serum cholesterol in the food animals and reducing the cholesterol level in the meat of the animal.

Livestock such as beef cattle, dairy cows, pigs, goats, sheep, chickens and horses can be immunized according the present invention. Still further, dairy animals such as milk cows and chickens may be immunized so as to produce dairy products that contain anti-ergosterol antibodies. The production of anti-ergosterol and their concentration in milk, or eggs in the case of chickens, will result in dairy products (for example, infant formula, milk, cheese, butter, ice cream, yogurt) that, when ingested orally will provide the recipient passive immunity against fungal diseases.

Additionally, the dairy products or antibodies refined from immune milk or eggs could be made into a douche for treating vaginal candidiasis. Further, gastrointestinal fungus infections are on the increase; gastrointestinal candidiasis is estimated to afflict 10% of the United States population. This problem is exacerbated by the chronic administration of antibacterial antibiotics such as penicillin, erythromycin, tetracycline, etc. Ingestion of dairy products obtained from dairy animals vaccinated against ergosterol would result in the harmless excretion of *Candida* and other fungal organisms. These products also could be applied topically for the treatment of fungal diseases of the skin. An additional benefit of these anti-ergosterol dairy products is the increased resistance to fungal degradation, thus increasing storage and shelf life, and reducing spoilage.

Immunization produces effective immunity in mammals against ergosterol. Since ergosterol is not a normal lipid constituent of mammalian tissues, but is found mainly in plants, fungi, and certain parasites, this immunization procedure results in production of a vaccine that provides protective immunity against fungi and parasites containing ergosterol.

A second aspect of the invention encompasses liposomal or other delivery compositions that contain ergosterol or ergosterol derivatives, and methods of use thereof. These compositions are useful for immunizing humans and animals for the treatment and prevention of fungal infection. In yet another embodiment of the present invention, liposome compositions may further contain lipid A.

Another aspect of the invention encompasses a diagnostic assay for determining whether a human or animal has a fungal infection by measuring antibodies to ergosterol. This aspect of the invention also encompasses a diagnostic kit for determining whether a human or animal has a fungal infection.

A further aspect of the invention relates to improved methods of synthesizing cholesterol and ergosterol derivatives, such as phosphatidylcholesterol and phosphatidylergosterol.

Accordingly, it is an object of the present invention to provide methods and compositions for the immunization of humans or animals against sterols.

It is another object of the present invention to provide methods and compositions for immunizing a human or animal against cholesterol and its derivatives.

It is another object of the present invention to provide methods and compositions for immunizing a human or animal against ergosterol and its derivatives.

It is yet another object of the present invention to provide methods and compositions for reducing the blood cholesterol level.

It is another object of the present invention to provide methods and compositions for increasing the resistance of a human or animal to fungal diseases.

It is yet another object of the present invention to provide methods and compositions for decreasing the cholesterol content in the meat of food animals.

It is another object of the present invention to provide methods and compositions for immunizing dairy animals against ergosterol.

It is yet another object of the present invention to provide dairy products that contain high concentrations of anti-ergosterol antibodies.

It is a further object of the present invention to provide a diagnostic assay and kit for determining whether a human or animal has a fungal infection.

It is yet another object of the present invention to provide improved methods of synthesizing cholesterol and ergosterol derivatives.

These and other objects, features and advantages of the present invention will become apparent after a review of the following detailed description of the disclosed embodiments and the appended claims.

BRIEF DESCRIPTION OF THE FIGURES

FIG. 1 depicts the structure of cholesterol.

FIG. 2 depicts the structure of ergosterol.

FIG. 7 depicts the structure of 5-Androsten-3β-OL-17β carboxylic acid.

FIG. 8 discloses the IgG reactivity of antisera against individual liposomal components.

FIG. 9 illustrates the time course of IgG response against phosphatidylcholesterol.

FIG. 10 illustrates anti-liposome activities of mice immunized with DMPC/DMPG/Phos-Chol/Chol/Lipid A liposomes.

FIG. 11 graphically illustrates activities of sera against cholesterol- and phosphatidylcholesterol-containing liposomes.

DETAILED DESCRIPTION

Figure 3:
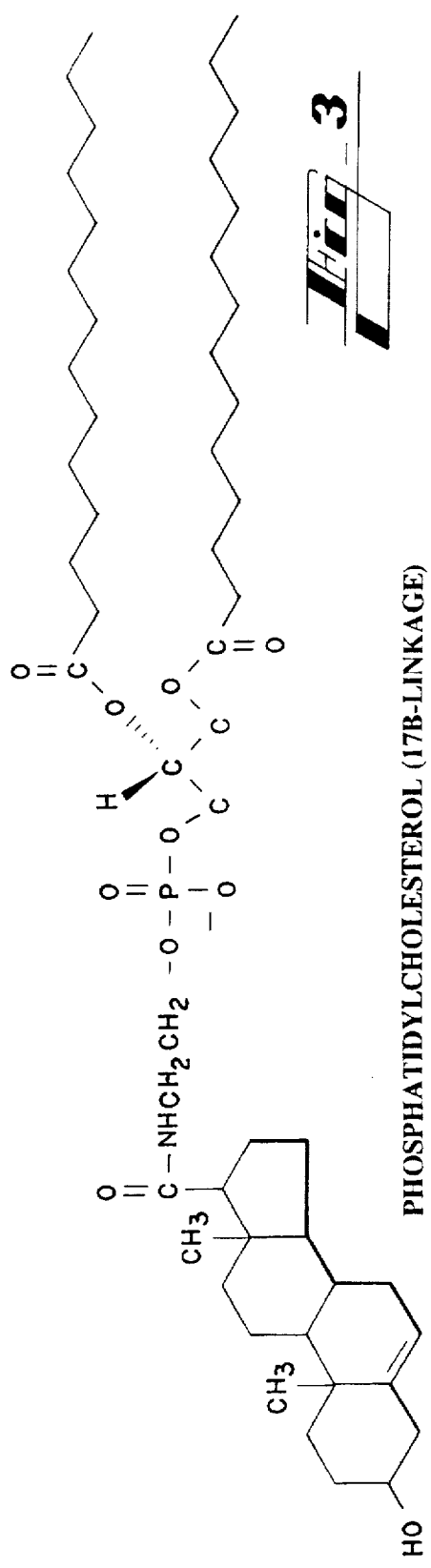
FIG. 3 depicts the structure of phosphatidyl-cholesterol (17β-Linkage).

The present invention is directed to methods and compositions for immunizing a human or an animal against sterols, and more specifically against cholesterol and/or ergosterol and derivatives of the two compounds. The present invention utilizes liposome and related delivery vehicle technology to effectively immunize the human or animal against the desired sterol.

The term "approximately" as used herein means within 5% of the stated number. For example, "approximately 1:2.5" means a ratio of approximately 1 part to approximately 2.5 parts, each component being approximately ±5% of the stated value.

Any delivery vehicle that can incorporate sterols, particularly either cholesterol or ergosterol or their derivatives, or a combination thereof, and which is capable of eliciting the production of antibodies directed against cholesterol or ergosterol when administered to humans and animals can be used in the present invention. Such delivery vehicles act primarily as antigen carriers, facilitating presentation of the sterol to the immune system, thereby eliciting or enhancing a immune response. It is presumed that any established method for inducing antibodies against substances or macromolecules theoretically could be adapted to inducing antibodies to cholesterol.

Cholesterol immunogenicity is enhanced by adjuvants (e.g., lipid A or other adjuvants), by altering the presentation of cholesterol, or by increasing the exposure of the cholesterol ring system. Also, cholesterol immunogenicity is enhanced by increasing the epitope density of the sterol used for immunization. It is possible to achieve high epitope densities of cholesterol using a variety of delivery vehicles, and by high density conjugation or association of cholesterol with proteins or other macromolecules. Delivery vehicles useful in the vaccines of the present invention include, but are not limited to, biocompatible-biodegradable, or biocompatible-nonbiodegradable liposomes, lipospheres, polymers, and slow release devices such as microspheres or microcapsules, and combinations thereof. These and similar delivery vehicles well known in the art may serve to deliver sterols, and more particularly cholesterol and/or ergosterol and/or their derivatives to humans or animals.

Standard methods of manufacturing and using liposomes are taught by Alving et al. (Preparation and Use of Liposomes in Immunological Studies, *Liposome Technology*, Vol. II, pages 157–175 (1984)), and Alving et al. (Preparation and Use of Liposomes in Immunological Studies, *Liposome Technology*, 2nd Edition, Vol. III, pages 317–343 (1993)), hereby incorporated by reference. Liposomes manufactured by standard methods are loaded with cholesterol (containing approximately 70% cholesterol) and optimally also contain lipid A as an adjuvant, and are prepared for injection as taught by Swartz et al. (Antibodies to cholesterol. *Proc. Nat. Acad. Sci.* 85:1902–1906, 1988) and Alving et al. (U.S. Pat. No. 4,885,256 issued 5 Dec. 1989), hereby incorporated by reference. It is to be understood that there are several formulations of cholesterol- or ergosterol-loaded liposomes that can be used to practice the present invention. Similar delivery vehicles are those delivery vehicles that are functionally equivalent in their ability to serve as carriers of sterols, such as cholesterol or ergosterol, and present the sterol to the immune system of individuals to which the compositions have been administered so as to elicit an immune response.

The compositions of the present invention may optionally include any adjuvant or mixture of adjuvants known to one skilled in the art capable of boosting or enhancing the immune response against cholesterol and ergosterol. Examples of adjuvants include, but are not limited to, lipophilic muramyl dipeptide derivatives incorporated into liposomes, nonionic block polymers, aluminum hydroxide or aluminum phosphate adjuvant, and mixtures thereof. A preferred adjuvant is lipid A.

When cholesterol is used in a vaccine which comprises the present invention, the serum cholesterol level of the immunized individual is reduced and the severity of atherosclerosis or atherosclerosis plaques is retarded. The anti-cholesterol vaccine consists of a formulation containing cholesterol; or cholesterol and phosphatidyl choline; or more particularly, cholesterol and dimyristoyl phosphatidyl choline together with a suitable delivery vehicle. The present invention may optionally contain a suitable adjuvant. The relative molar ratio between the cholesterol and phosphatidyl choline or dimyristoyl phosphatidyl choline is within the range of approximately 0.75:1 to 9:1. In a preferred embodiment, the ratio of cholesterol to phosphatidyl choline or dimyristoyl phosphatidyl choline is 5:2.

Figure 4:
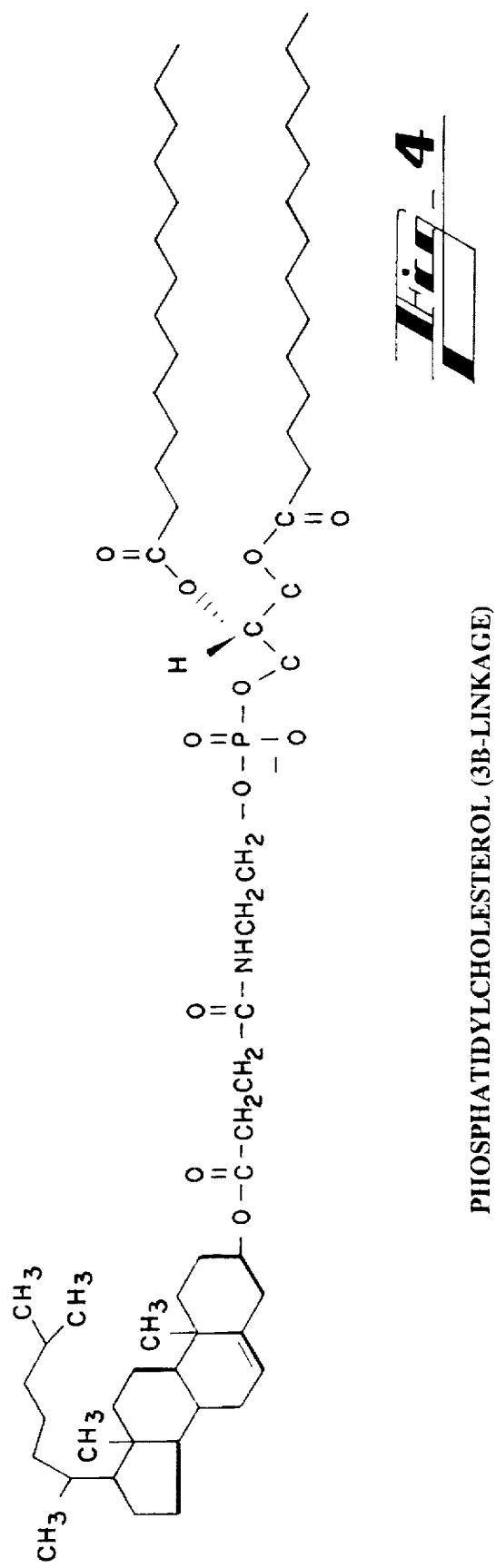
FIG. 4 depicts the structure of phosphatidyl-cholesterol (3β-Linkage).
Figure 5:
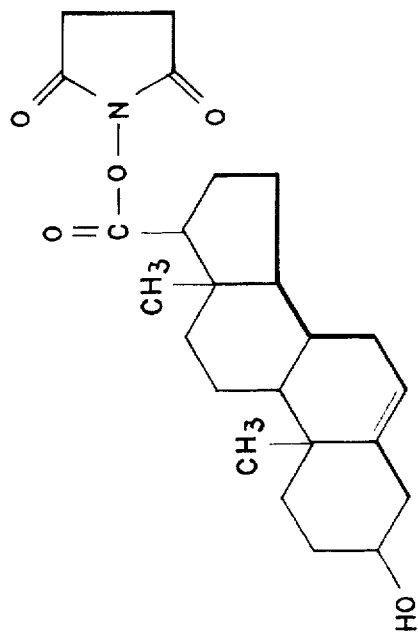
FIG. 5 depicts the structure of cholesterol ester.

It is to be understood that derivatives of cholesterol may also be used in the vaccine of the present invention. The cholesterol derivatives that may be used in the present invention include, but are not limited to, cholesteryl oleate, vitamin D2, cholesteryl myristate, 4-cholesten-3-one, 5-Androsten-3β-OL-17β amine, phosphatidylcholesterol (17β-Linkage and 3β-Linkage), and cholesterol ester. 17β-Linkage phosphatidylcholesterol ($C_{53}H_{44}NO_{10}P$) has two formal names: N-(5-Androsten-3β-OL-17β-amino) dimyristoylphosphatidylethanolamine, and 1,2-dimyristoyl-rac-glyceryl-3-phosphoryl-17-(3β-hydroxy norpregn-5-ene). 3β-Linkage phosphatidylcholesterol has the following formal name: N-[cholest-5-en-3β (succinylamido)] dimyristoyl-phosphatidylethanolamine. Cholesterol ester ($C_{24}H_{33}NO_5$) has two formal names: 3β-hydroxyetiochol-5-enic 17β-(N-hydroxy-succinimide ester), and Androst 5-en-3-OH-17β-(N-hydroxy-succinimide ester). The structures of phosphatidylcholesterol (17β-Linkage and 3β-Linkage) and cholesterol ester are illustrated in FIGS. 3, 4, and 5.

Regarding the efficacy of cholesterol as an to immunogen, cholesterol is less effective than proteins. The cause of this lesser ability of cholesterol to stimulate an immune response may be related to the fact that cholesterol, whether in liposomes or natural membranes, is buried in the membrane and may not be generally accessible. Cholesteryl esters have been synthesized and are commonly available in which the 3β-hydroxyl is the point of linkage to fatty acids. Compounds have also been synthesized where phospholipids are linked to the 3β-hydroxyl.

Accordingly, it is desirable to utilize a molecule having the phospholipid linked to the hydrophobic tail of cholesterol, leaving the cholesterol headgroup (3β-hydroxyl) intact. Although not wanting to be limited by the following hypothesis, it is believed that the phospholipid portion of a phosphatidylcholesterol molecule and a phosphatidylergosterol molecule result in an improved presentation of cholesterol or ergosterol in a liposome format (via greater exposure of the cholesterol or ergosterol portion of the molecule) and increase sensitivity in both the Enzyme-linked Immunosorbent Assay ("ELISA") and glucose release assays. Phosphatidylcholesterol has been previously synthesized, however its synthesis required a complex, multistep method as described in Hara et al., *Immunochemical Properties of Phosphatidylcholesterol and its Homologue*, Chemistry and Physics of Lipids, 23:7–12 (1979).

The method described in Example VI is another aspect of the present invention, and is a much simpler method for conjugating cholesterol, or a ring structure that looks like cholesterol, to a phospholipid to "force" the main ring system of cholesterol out of its normal position within the bilayer.

Briefly described, the method of synthesizing phosphatidylcholesterol (17β-Linkage) comprises reacting dimyristoylphosphatidylethanolamine ("DMPE") with the N-hydroxysuccinimide ester of 5-Androsten-3β-OL-17β-carboxylic acid. The route of synthesis is to first convert 5-Androsten-3β-OL-17β-carboxyl acid to the N-hydroxysuccinimide ester. 5-Androsten-3β-OL-17β-carboxylic acid has the same ring system as cholesterol but has replaced at the 17-carbon position a free carboxyl group, and is available from Sigma Chemical Co., of St. Louis, Mo. The structure of 5-Androsten-3β-OL-17β-carboxylic acid is illustrated in FIG. 7. Another name for 5-Androsten-3β-OL-17β-carboxylic acid is 3β-Hydroxyetiochol-5-enic 17-β Acid. The N-hydroxysuccinimide ester is then reacted with the DMPE to form the phosphatidylcholesterol (17β-Linkage). The above reaction is more fully described in Example VI. Although phosphatidylcholesterol may be synthesized by any means known in the art, the preferred method of synthesizing phosphatidylcholesterol (17β-Linkage) is described in Example VI.

Another aspect of the present invention is a method of synthesizing phosphatidylcholesterol (3β-Linkage) from cholesterol. Briefly described, the method of synthesizing phosphatidylcholesterol (3β-Linkage) comprises reacting cholesterol with succinic anhydride to produce cholesterol hemisuccinate, reacting cholesterol hemisuccinate with N-hydroxysuccinimide to form cholesterol-N-hydroxysuccinimide ester, and condensing the cholesterol-N-hydroxysuccinimide ester with dimyristoylphosphatidylethanolamine ("DMPE"). The reaction is more fully described in Example XII. Although Example XII specifically describes a method of synthesizing phosphatidylergosterol, the same method can be used for synthesizing phosphatidylcholesterol (3β-Linkage).

In one embodiment of the synthesis of phosphatidylcholesterol (3β-Linkage), instead of reacting cholesterol with succinic anhydride in Step 1 to form cholesterol-hemisuccinate, cholesterol-hemisuccinate may be purchased from Steraloids, Inc. (Wilton, N.H.). Reacting the purchased cholesterol-hemisuccinate with NHS and then subsequently with DMPE would follow the method as described in Example XII.

In another embodiment of the synthesis of phosphatidylcholesterol (3β-Linkage), instead of reacting cholesterol with succinic anhydride in Step 1, cholesterol could be reacted with glutaric anhydride. Reacting cholesterol with glutaric anhydride would lengthen the spacer between the sterol ring and the phospholipid, thus altering the immunogenicity, and perhaps other characteristics of the analog.

Ergosterol-containing compositions useful as vaccines for immunization are made as described above except the amount of unconjugated ergosterol incorporated into the liposomes preferably is approximately 1/13 as much as cholesterol. Thus, the relative molar ratio between ergosterol and phosphatidyl choline or dimyristoyl phosphatidyl choline is approximately 0.058:1 to approximately 0.69:1. A preferred ratio is 0.19:1. Lipids useful in the present invention include those which form smectic mesophases. The human or animal to which the anti-ergosterol vaccine is administered can be any human or animal capable of producing antibodies suffering from a fungal infection, or any human or animal capable of producing antibodies, to be immunized against fungal infections.

Figure 6:
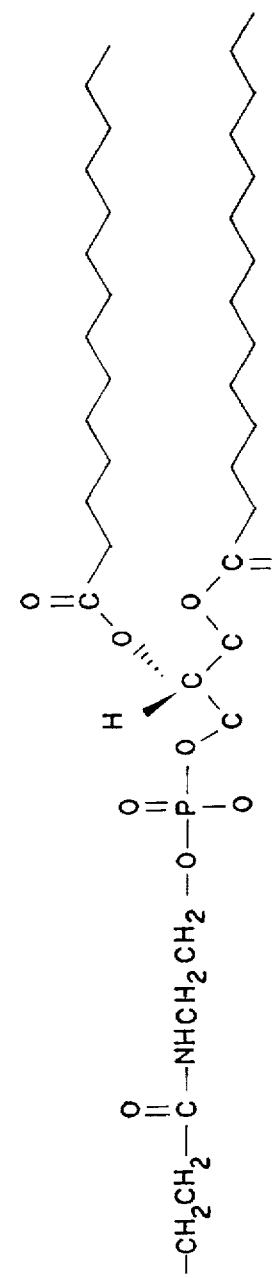
FIG. 6 depicts the structure of phosphatidyl-ergosterol.

It is to be understood that ergosterol derivatives may also be used in the vaccine of the present invention. The ergosterol derivatives that can be used in the present invention include, but are not limited to, phosphatidylergosterol. The formal name of phosphatidylergosterol is the following: N-[(3β,22E)-ergosta-5,7,22-trien-3-(succinylamido)] dimyristoyl-phosphatidylethanolamine. The structure of phosphatidyl-ergosterol is illustrated in FIG. 6. The phosphatidyl group of phosphatidyl-ergosterol increases the exposure of the ergosterol ring system in liposomal bilayers to improve the immunogenicity of ergosterol administered in a vaccine composition.

Another aspect of the present invention is a method of synthesizing phosphatidylergosterol from ergosterol. Briefly described, the method of synthesizing phosphatidylergosterol comprises reacting ergosterol with succinic anhydride to produce ergosterol hemisuccinate, reacting the erosterol hemisuccinate with N-hydroxysuccinimide to form ergosterol-N-hydroxysuccinimide ester, and condensing the ergosterol-N-hydroxysuccinimide ester with DMPE. The reaction is more fully described in Example XII.

Although not wanting to be bound by the following theory, it is believed that liposomes containing ergosterol, and optionally lipid A, of the present invention induce the production of antibodies to ergosterol or other forms of immunity to ergosterol. After immunization with the vaccine, T helper lymphocytes will serve as intermediary cells in the production of IgG antibodies against ergosterol and for the generation of immunological memory against ergosterol. Additionally, other forms of immunity can be induced, including IgM and IgA antibodies, and cytotoxic T lymphocytes having specificity against ergosterol.

One of the major hurdles in producing such a vaccine is the generation of highly specific immunity. It is well-known that antibodies generated against sterol compounds conjugated to carrier molecules often cross-react to varying degrees with sterols having similar structures. This cross-reactivity can be even greater with a sterol structure that was not used for immunization than with the structure that was used for immunization, a concept reviewed elsewhere (Franek, M., Structural aspects of sterol-antibody specificity, *J. Steroid Biochem.* 28:95–108, 1987). The basis for cross-reactivity of such antibodies lies in the fact that all of the target compounds against which the antibodies are directed have a similar cyclopentanoperhydrophenanthrine-like multiple ring sterol structure. In the present invention, it is evident from observing the structures of cholesterol and ergosterol, shown in FIGS. 1 and 2, respectively, that many epitopes on the ring structure are similar or identical, and there is no way to predict which epitopes will actually be immunodominant.

Antibodies against ergosterol which have greater specificity and reduced cross-reactivity may be produced by blocking the 3-hydroxy moiety. In theory, because the 3-hydroxy moiety of cholesterol is the only polar group on the molecule, and is therefore the group most likely to be exposed to the water interface of a lipid bilayer, it is believed this group lies within the immunodominant group of cholesterol. Blocking this group on ergosterol drives the immunological specificity more toward recognition of other groups on the ring structure thereby providing greater immunological specificity for ergosterol. The 3-hydroxy group of ergosterol can be blocked by a variety of methods, including adding esterified groups or other chemical additions that react directly at the 3-hydroxy site. Additionally, other groups added to sites very close to the C-3 region might also exert steric hindrance that would block production of immunity at that location. Similarly, molecules that react directly with the ergosterol molecule, such as saponins or macrolide polyene antibiotics (e.g., filipin, amphotericin, or nystatin) also have the intended effect of orienting the ergosterol molecule in such a way as to block immunity to the C-3 site of the A ring of ergosterol and thereby promote specific immunological recognition at other ring sites.

Another embodiment of the present invention encompasses an accurate, rapid and convenient diagnostic assay for detecting the presence and quantity of antibodies directed against ergosterol, which indicates whether a human or animal has a fungal infection. The diagnostic assay comprises removing a sample body fluid from the human or animal, and measuring the presence and quantity of anti-ergosterol antibodies present in the body fluid. The presence and quantity of anti-ergosterol antibodies would be measured by standard immunology techniques well known in the ordinary skill of the art. Such standard immunology techniques include, but are not limited to, competitive or non-competitive assays, immobilized or non-immobilized assays, and direct or indirect assays.

The presence and quantity of antibodies directed against ergosterol is measured by various immunoassay techniques employing one or more antibodies specific for unique antigenic determinants present on the antibodies directed against ergosterol ("anti-ergosterol antibodies"). In the immunoassays, the reactivity between antibodies directed against ergosterol and an antibody specific thereto is determined by observing the formation of complexes of the two antibodies by using fluorescent, radioactive, or enzymatic labels including bio- or chemiluminescent labels. The enzyme labels which may be used in the present invention include, but are not limited to, color producing enzymes such as horse radish peroxidase ("HRP") and alkaline phosphatase ("AP"), and light producing enzymes such as luciferase. The antibodies specific for the anti-ergosterol antibodies can be used in a number of different diagnostic tests. Such assays include, but are not limited to, ELISA, Western blot, radioimmunoassay ("RIA"), bioluminescent assay, and chemiluminescent assay. Such immunoassays are well-known in the art; protocols are found, for example, in *Current Protocols in Immunology*. An example of such an immunoassay is described in Example IX.

Yet another embodiment of the present invention encompasses an accurate, rapid and convenient diagnostic assay kit for detecting the presence and quantity of antibodies directed against ergosterol. The kit includes the antibody or antibodies directed against unique antigenic sites present on anti-ergosterol antibodies. The kit also includes a signal producing system, for example, a conjugate of a label and a specific binding partner for the antibodies directed against the anti-ergosterol antibodies. The label may consist of fluorophores, chemophores, radionuclides, color-producing enzymes, and paramagnetic metals. The specific binding partner may include polyclonal or monoclonal antibodies reactive with the antibodies directed against the anti-ergosterol antibodies, or any molecule capable of irreversible binding to the antibody molecule itself.

The particular components of the kit correspond to the particular immunoassay procedure being employed. In one embodiment, the diagnostic kit may include a polyclonal or monoclonal antibody of the present invention directed against anti-ergosterol antibodies, wherein the polyclonal or monoclonal antibody has been conjugated with a suitable marker capable of producing a detectable signal. To carry out the assay, the test sample is placed in contact with the antibody-marker conjugate. Thereafter, the complexed components are separated from the free components of the assay, and then the signal produced by the marker is detected and quantified in either the bound or free components of the immunoassay reaction. The assay components may include an insoluble matrix on which the antibody is covalently or noncovalently coupled, buffers to maintain the desired pH of the immunoassay reaction, and binding media to dilute the fluid sample. The kit may also include reagents required for the marker to produce a detectable signal, such as an appropriate enzyme reagent for ELISA assay, or agents to enhance the detectable signal.

In another embodiment, the diagnostic kit may include a primary polyclonal or monoclonal antibody directed against anti-ergosterol antibodies and a secondary antibody directed against the primary antibody, wherein the second antibody is conjugated to a suitable marker capable of producing a detectable signal. As in the embodiment of the assay it discussed above, this kit embodiment also may include other additional components. To carry out the assay, a test sample is placed in contact with the primary antibody and then the complexed components are separated from the free components. Thereafter, the complexed components are placed in contact with the labeled secondary antibody which specifically couples with the primary antibody bound to the anti-ergosterol antibody. After the unbound secondary antibody is separated from the complexed components of the assay, the signal produced by the label is measured in either the bound or free components of the assay reaction.

In yet another embodiment, the diagnostic kit may include ergosterol and an antibody directed against anti-ergosterol antibodies which is conjugated to a suitable marker capable of producing a detectable signal. As above, this embodiment may also include other additional components. To carry out the assay, a test sample is placed in contact with the ergosterol and then the complexed components separated from the free components. Thereafter, the complexed components are placed in contact with the labeled antibody directed against anti-ergosterol antibodies, which specifically couples with the anti-ergosterol antibody bound to the ergosterol. After the bound components are separated from the unbound components, the signal produced by the label is measured in either the bound or free components of the assay reaction.

This invention is further illustrated by the following examples, which are not to be construed in any way as imposing limitations upon the scope thereof. On the contrary, it is to be clearly understood that resort may be had to various other embodiments, modifications, and equivalents thereof which, after reading the description herein, may suggest themselves to those skilled in the art without departing from the spirit of the present invention and/or the scope of the appended claims.

EXAMPLE I

Vaccine against Cholesterol

The cholesterol vaccine comprises the following as the active ingredients:

A. a delivery vehicle and

B. either,
  (i) cholesterol; or
  (ii) cholesterol and an adjuvant; or
  (iii) cholesterol, phosphatidyl choline and an adjuvant; or
  (iv) cholesterol, dimyristoyl phosphatidyl choline and an adjuvant; or
  (v) cholesterol and phosphatidyl choline;
  (vi) cholesterol and dimyristoyl phosphatidyl choline; or
  (vii) dimyristoylphosphatidylglycerol It is to be understood that cholesterol derivatives may also be used in the vaccine of the present invention. More particularly, phosphatidylcholesterol (17β-Linkage), phosphatidylcholesterol (3β-Linkage), and cholesterol ester may be used in the above vaccine.

Liposomes are manufactured by standard methods in which liposomes loaded with cholesterol (containing approximately 70% cholesterol) and optimally also containing lipid A as an adjuvant are prepared for injection as taught by Swartz et al. (Antibodies to cholesterol. *Proc. Nat. Acad. Sci.* 85:1902–1906, 1988) and Alving et al. (U.S. Pat. No. 4,885,256 issued 5 Dec. 1989), both of which incorporated by reference. It is to be understood that there are several formulations of cholesterol- or ergosterol-loaded liposomes that can be used to practice the present invention.

EXAMPLE II

The preferred liposomes used for immunization against cholesterol contain dimyristoylphosphatidylcholine ("DMPC")/cholesterol ("chol")/ dimyristoylphosphatidylglycerol ("DMPG")/lipid A (molar ratio approximately 0.9/2.5/0.1/0.02 (71% CHOL) for rabbits or humans, or approximately 0.9/0.75/0.1/0.02 (43% CHOL) for humans, where the molarity of lipid A refers to lipid A phosphate). Lipid A from the chloroform-soluble fraction obtained from *Shigella flexneri* may be used. The total dose of lipid A injected as part of the 71% cholesterol liposomes was 50 µg lipid A. The liposomal cholesterol concentration is described as a percentage, and this is calculated as mol% with reference to (DMPC+DMPG); e.g., a cholesterol/(DMPC+DMPG) ratio of 0.75/1 is 43 mol%, and 2.5/1 is 71 mol%.

EXAMPLE III

Enzyme-linked Immunosorbent Assay ("ELISA").

ELISAs were performed by using crystalline cholesterol as an antigen on the bottoms of the wells of microtiter plates. Crystalline cholesterol was coated onto the surface of wells in polystyrene plates (Immunlon 96, "U" bottom, Dynatech Laboratories, Alexandria, Va.) by addition of an ethanolic solution and evaporation of the solvent by air under a fume hood. Plates were further dried under high vacuum and stored at −20° C. when not used the same day. Plates were blocked by addition of phosphate-buffered saline (PBS: 137 mM NaCl/2.7 mM KCl/9.6 mM phosphate, pH7.2) containing 10% heat-inactivated (56°, 30 min) fetal bovine serum ("FBS") (M.A. Bioproducts, Walkersville, Md.). This was accomplished by washing the wells three times for 10 min each. Fifty microliters of ascites fluid containing monoclonal antibodies, diluted in PBS containing 10% FBS, was added to the wells and incubated 1 hr at room temperature. Plates were then washed three times for 5 minutes each with PBS. Fifty microliters of goat anti-mouse IgM (mµ-chain) alkaline phosphatase conjugate (Kirkegaard and Perry Laboratories, Gaithersburg, Md.) at 1 microgram per ml in PBS containing 10% FBS was added to the wells and incubated 1 hour 5 at room temperature. Plates were again washed three times for 5 minutes each PBS. Fifty microliters of the substrate, p-nitrophenyl phosphate at 2 mg/ml in diethanolamine buffer (Kirkegaard and Perry Laboratories) was added to the well and incubated 30 minutes at room temperature. Plates were scanned for optical activity at 405 nm using a Titertek Multiscan (Flow Laboratories). Values reported were adjusted by subtracting value in blank wells that lacked both antigen and monoclonal antibody.

EXAMPLE IV

An experiment designed to determine the feasibility of ameliorating diet-induced hypercholesterolemia and atherosclerosis in rabbits was performed. Groups of rabbits were immunized while other groups were not immunized against cholesterol; at least one group of immunized and one group of nonimmunized rabbits were fed a diet rich in cholesterol. The immunization process ameliorates the hypercholesterolemia and atherosclerosis that is expected to be produced by the cholesterol-rich diet. The experimental results from the rabbit experiment described below provides substantive evidence in support of our prediction by demonstrating that the 1% cholesterol diet causes a dramatically increased serum cholesterol level within 1 week (6 weeks after initial immunization in those rabbits that were immunized), and the cholesterol continues to rise over the second week (7 weeks after initial immunization was started in the immunized animals). However, the increased level of diet-induced cholesterol is 30% less elevated in the animals (Group II) that were immunized against cholesterol.

Immunization Protocol

Four groups of rabbits were either immunized with liposomes containing 71 mol % cholesterol, or were not immunized. Immunization was performed either intramuscularly or intravenously every two weeks for 6 weeks. The immunization procedure routinely induced antibodies to cholesterol in rabbits, as determined by ELISA or by complement-induced immune damage to high-cholesterol liposomes as taught by Swartz et al., Antibodies to cholesterol. *Proc. Nat. Acad. Sci.* 85:1902–1906, 1988, and Alving et al., U.S. Pat. No. 4,885,256 issued 5 Dec. 1989, both of which are incorporated by reference.

Experimental Diets

At week 6 after immunization, the experimental diets were initiated. The diets consisted either of ordinary rabbit chow or a 1% cholesterol diet (obtained from Bioserve). Four groups and two subgroups of animals were employed: Group I, 4 rabbits, not immunized, fed normal diet; Group IIa, 4 rabbits, immunized intramuscularly, fed 1% cholesterol diet; Group IIb, 2 rabbits, immunized intravenously, fed 1% cholesterol diet; Group III, 4 rabbits, not immunized, fed normal diet; Group IVa, 4 rabbits, immunized intramuscularly, fed normal diet; Group IVb, 2 rabbits, immunized intravenously, fed normal diet.

Results

The results of this experiment, shown in Table I, demonstrate that the high cholesterol diet invariably caused elevated serum cholesterol values. However, two weeks after initiating the diet (week 7) the elevation of cholesterol in the immunized group (Group II) was 30% less than the elevation of cholesterol in the nonimmunized group (Group I).

TABLE 1

Reduction of Diet-Induced Hypercholesterolemia in Rabbits Immunized Against Cholesterol.

| Group[a] | High Cholesterol Diet[b] | Immunized[c] | Bleeding Time (Weeks) | Serum Cholesterol (mg/dl) | Increase Compared to Week 5 | Reduced Increase (%) |
|---|---|---|---|---|---|---|
| I | − | − | 5 | 76 | | |
| II | − | + | 5 | 62 | | |
| III | − | − | 5 | 73 | | |
| IV | − | + | 5 | 83 | | |
| I | + | − | 6 | 775 | 699 | |
| II | + | + | 6 | 797 | 734 | |
| III | − | − | 6 | 64 | | |
| IV | − | + | 6 | 68 | | |
| I | + | − | 7 | 1205 | 1129 | |
| II | + | + | 7 | 952 | 790 | 30 |
| III | − | − | 7 | 74 | | |
| IV | − | + | 7 | 62 | | |

[a]Data shown are means of results (Group I, 4 rabbits; II, 6 rabbits; III, 4 rabbits; IV, 6 rabbits).
[b]The 1% cholesterol diet was initiated at the 5 week time point after starting the experiment.
[c]The immunization against cholesterol was initiated at 0 weeks.

The present invention also encompasses vaccines for immunizing or hyperimmunizing a human or animal against other sterols, such as ergosterol. Methods similar to those described above may be used to prepare vaccines to other sterols. The preferred general composition of the vaccine for immunizing a human or animal against ergosterol is shown in the following Example.

EXAMPLE V

Antigenicity in Mice of Cholesterol and Sterol Analogs Administered in Liposomes Containing Lipid A A number of animal species, including man, have naturally-occurring antibodies ("IgM") reactive with crystalline cholesterol. In experimental animals exposed to a vaccine composed of dimyristoylphosphatidylcholine ("DMPC") and dimyristoylphosphatidylglycerol ("DMPG") with monophosphoryl lipid A as adjuvant, titers of anti-cholesterol IgM antibodies increase five to a thousand-fold, depending on the level of cholesterol in the vaccine, the number of vaccinations, and the amount of adjuvant. The following study is designed to test the feasibility of stimulating a longer lasting immune response to cholesterol as evidenced by the production of IgG antibodies and to determine if these antibodies (or differences in antibody isotype) change levels of circulating cholesterol.

Critical to the success of a vaccine against hypercholesterolemia is the ability of the antisera to react with cholesterol that is presented in different conformations. Previous studies using liposomes containing 43 or 71% cholesterol along with DMPC and DPMG suggest that how cholesterol is immunologically presented in these two types of liposomes may be different: cholesterol in liposomes containing 43% cholesterol is less apt to form crystals compared to liposomes containing 71% cholesterol. Crystals of cholesterol have been demonstrated within the bilayers of cholesterol/phospholipid dispersions similar to ours (Collins, J. J. et al. (1982) *J. Lipid Res.* 23:291–298). Which presentation form of cholesterol predominates or is most important in the pathology of hypercholesterolemia or atherosclerosis is not currently known. Antigens that generate antibodies which react with different regions of the cholesterol molecule may help determine which epitope to use in a vaccine against hypercholesterolemia.

As shown in Example VI, we synthesized a cholesterol analog, the trivial name of which is phosphatidylcholesterol, in which the hydrophobic tail of a cholesterol analog ring system is covalently linked to the headgroup of a phospholipid. An antigen such as phosphatidylcholesterol, used in a liposome format, may increase the exposure of the "cholesterol" ring system to the immune system and increase the antigenicity of the ring system. Three important outcomes from exposure to such an analog are possible: (1) stimulation of higher titers of IgM, (2) stimulation of a different antibody response, such as IgG, in addition to the usual IgM, and (3) generation of a longer lasting immunologic memory response. Exposure of the ring system may not normally occur, which could account for the fact that cholesterol is not a potent immunogen. In this study we tested only the antigenic characteristics of phosphatidylcholesterol. It is clear, however, that a balance exists between generation of an effective immune response against cholesterol (efficacy) and induction of a harmful autoimmune response (toxicity) for such a vaccine to be feasible.

Accordingly, the following study is designed to assess the immunogenicity of different cholesterol or sterol analogs for use in a vaccine to prevent hyper-cholesterolemia. Briefly summarized, several sterols such as cholesterol, vitamin D2, cholesteryl oleate, cholesteryl myristate, 4-cholesten-3-one, and phosphatidylcholesterol (17β-Linkage) and (3β-Linkage), are incorporated into liposomes containing DPMC (1.8), DMPG (0.2), Chol (1.5) (mol/mol) and lipid A (25 to 200 μg/μmol, preferably 25 μg/μmol phospholipid) so that the phospholipid concentration remains constant. These liposomes are inoculated into BALB/c mice i.p. at day 0 and day 14. Mice are bled at day 14 and day 21 and antibodies specific for the antigen are assessed by ELISA using the antigen itself or crystalline cholesterol.

Methods

Synthesis of Phosphatidylcholesterol

The synthesis of phosphatidylcholesterol was carried out in two steps: (1) conversion of 5-Androsten-3β-OL-17β-carboxylic acid to the 17β-N-hydroxysuccinimide (NSH) ester and (2) formation of an amide by reacting the NHS ester with the amine of dimyristoyl-phosphatidylethanolamine ("DMPE"). The synthesis of phosphatidylcholesterol is more fully described in Example VI.

Liposome Preparation

Multilamellar vesicles ("MLV") are produced by aliquoting DMPC:DMPG:Cholesterol, 9:1:7.5 (mol/mol), and lipid A at 25 to 200 μg/μmol phospholipid into a round bottom flask. The mixture is rotary evaporated, desiccated, and hydrated in sterile, deionized water. Lipids are lyophilized and reconstituted in PBS to 10 mM with respect to phospholipids and assayed for total phosphorous.

Antibody Production

Male BALB/c mice, 6–8 weeks old, are bled and then immunized with 0.1 ml liposomes containing 1 μmol total phospholipid and 25–200 μg monophosphoryl lipid A ip. At 14 day intervals, mice are bled and sera collected. Mice are boosted with the same liposome innoculum at 2-week intervals.

ELISA Assays of Antisera

To determine anti-cholesterol antibody titers, three types of ELISA protocols are used that vary only in the form of the lipid antigen plated: (1) a "crystalline" lipid where lipid is dissolved in ethanol, is added to the ELISA plate and the ethanol is evaporated, leaving crystalline lipid in the well; (2) a liposome, where MLV containing the lipid antigen serves as the plated antigen; and (3) sandwich assay where a monoclonal anti-liposome or anti-cholesterol is plated, liposomes are added, and then serum is added. Standard ELISA reagents are used in all cases, except that detergents are omitted to prevent removal of lipid antigens from the plate. Horseradish peroxidase/(2,2'-azino-di[-3-ethyl-benzthiazolinesulfonate ("ABTS") is the enzyme/substrate system.

Complement-Dependent Immune Lysis Assay of Antisera

This assay measures antibody-mediated, complement-dependent release of encapsulated glucose from liposomes. Released glucose is measured spectrophotometrically using a Tris-buffered assay reagent containing hexokinase, glucose-6-phosphate dehydrogenase, ATP, and NADP. This particular assay is a measurement of antibody functional activity, rather than particle (antibody) detection.

Results and Conclusions

All sterol antigens induced antibodies that reacted with cholesterol, but reaction with the specific immunizing antigen was markedly higher. Detailed evaluation of cholesterol and phosphatidylcholesterol (17β-Linkage) demonstrated differences in the immunogenicity of the compounds. The most significant difference was that antibodies detected by ELISA from mice vaccinated with the cholesterol vaccine were mainly IgM, with a little IgG. In contrast, as shown in FIG. 8, the phosphatidylcholesterol vaccine induced a high level of specific IgG antibodies. Further, as shown in FIG. 9, specific anti-phosphatidylcholesterol IgG was produced when mice were inoculated with liposomes containing 10 mol % phosphatidylcholesterol. FIG. 9 also shows that the level of IgG produced increased with a booster inoculation. Serum was tested in a solid-phase ELISA using phosphatidylcholesterol as antigen, and control serum was generated by inoculating mice with liposomes lacking phosphatidylcholesterol.

In addition, the antisera from mice vaccinated with phosphatidylcholesterol could detect cholesterol present in liposomes containing 43% cholesterol as well as 71% cholesterol, and were equally as active against liposomes containing phosphatidylcholesterol in a complement-dependent immune lysis assay. As shown in FIG. 10, the antiserum generated by liposomes containing phosphatidylcholesterol lysed all three types of test liposomes containing different presentations of cholesterol, although it reacted 5–7 times better against liposomes containing 5 mol % phosphatidylcholesterol, compared to liposomes containing 43 or 71 mol % cholesterol and no phosphatidylcholesterol. In the above antibody-dependent immune lysis assays, a release greater than 5% indicates a positive reaction. Also, monoclonal antibodies ("IgM") prepared against 71% cholesterol in liposomes reacted with only the 71% liposomes in this assay, and not with 43% or 43% containing phosphatidylcholesterol.

As shown in FIG. 11, antisera generated against liposomes containing different amounts or presentations of cholesterol reacted best against test liposomes containing their respective immunogens. The test liposomes contained or lacked 5 mol % phosphatidylcholesterol. The antisera were tested using a complement-dependent immune lysis assay, wherein a release greater than 5% indicated a positive reaction. FIG. 11 shows that antisera from mice inoculated with liposomes containing only 5 mol % phosphatidylcholesterol gave maximal release, whether or not cholesterol was present in the innoculum. Only monoclonal antibodies raised against liposomes containing 71 mol % cholesterol resulted in maximal release: sera raised against 43 mol % liposomes resulted in only half-maximal release.

Therefore, this study shows that liposomal phosphatidylcholesterol induces significant amounts of IgG in addition to IgM. In contrast, cholesterol and other sterols induce primarily IgM. Also, antisera raised against liposomes containing phosphatidylcholesterol and either 43 mol % cholesterol or no cholesterol released significant amounts of glucose from liposomes containing only 5 mol % phosphatidylcholesterol, showing significant specificity and sensitivity for the phosphatidylcholesterol antigen. Anti-phosphatidylcholesterol antisera also reacted against liposomes containing 43% or 71% cholesterol, although to a lesser extent, indicating specificity for cholesterol that is presented in different forms. Further, more than 5 mol % phosphatidylcholesterol in liposomes containing 43 mol % cholesterol resulted in leaky liposomes in the antibody-mediated immune lysis assay. Bilayer disruption due to different integration pattern of the "cholesterol" ring system of phosphatidylcholesterol may account for this leakiness.

The above data suggests that antibodies prepared against phosphatidylcholesterol (17β-Linkage) react with a different epitope on cholesterol than the monoclonal. Since the phosphatidylcholesterol generated IgG antibodies which could recognize cholesterol in several different presentations, it may be the molecule of choice for a vaccine against cholesterol.

EXAMPLE VI

Brief Summary of the Synthesis of N-(5-Androsten-3β-OL-17β-Amido) Phosphatidylethanolamine, the Trivial Name of which is Phosphatidylcholesterol (17β-Linkage)

It is desirable to utilize a molecule having the phospholipid linked to the hydrophobic tail of cholesterol, leaving the cholesterol headgroup (3β-hydroxyl) intact. Phosphatidylcholesterol has been previously synthesized. However, its synthesis has required a complex, multistep method as described in Hara et al., *Immunochemical Properties of Phosphatidylcholesterol and its Homologue*, Chemistry and Physics of Lipids, 23:7–12 (1979). The following method uses a much simpler method to conjugate cholesterol, or a ring structure that looks like cholesterol, to a phospholipid in order to "force" the main ring system of cholesterol out of its normal position within the bilayer.

Briefly described, dimyristoylphosphatidyl-ethanolamine ("DMPE") is reacted with the N-hydroxysuccinimide ester of 5-Androsten-3β-OL-17β-carboxylic acid to form phosphatidylcholesterol (17β-Linkage). The route of synthesis of phosphatidylcholesterol is to first convert 5-Androsten-3β-OL-17β-carboxylic acid to the N-hydroxysuccinimide ester. 5-Androsten-3β-OL-17β-carboxylic acid has the same ring system as cholesterol but has replaced at the 17-carbon position a free carboxyl group, and is available from Sigma Chemical Co., of St. Louis, Mo. The structure of 5-Androsten-3β-OL-17β-carboxylic acid is illustrated in FIG. 7. Another name for 5-Androsten-3β-OL-17β-carboxylic acid is 3β-Hydroxyetiochol-5-enic 17-β Acid. The N-hydroxysuccinimide ester is then reacted with the DMPE to form the phosphatidylcholesterol (17β-Linkage). The appropriate reaction and purification conditions are as follows:

Synthesis of Androst 5-en-3-OH-17β-(N-hydroxy Succinimide Ester)

The following reaction is conducted in tetrahydrofuran ("THF"). Briefly stated, Androst 5-en-3-OH-17β-(N-hydroxysuccinimide ester) (the cholesterol ester) is synthesized by reacting approximately one mole of 5-Androsten-3β-OL-17β-carboxylic acid (318.4 g/mol), with approximately one to one and one half moles of N-hydroxysuccinimide ("NHS":115.1 g/mole), with approximately one mole of catalyst, dicyclohexylcarbodiimide ("DCC": 206.3 g/mole). The reaction steps are as follows:

Step 1: Add 1.59 g of 5-Androsten-3β-OL-17β-carboxylic acid (Sigma Chemical Company, St. Louis, Mo.) and 0.575 g NHS (Aldrich, Milwaukee, Wis.) to a 125-ml Erlenmeyer flask. Add approximately 65 ml THF to dissolve both compounds. Place flask on heater/stirrer and set heater to setting 3 (moderate heat) and mix with magnetic stir bar. Step 2: Heat crystalline DCC (Aldrich, Milwaukee, Wis.) in a 45° C. water bath to melt the crystals. Take approximately 825 µL (1.03 g @ 1.247 g/ml) of the liquid DCC and add it to the mixture of Step 1 using a 1-ml glass pipet. Heat the pipet used to add the liquid DCC to keep the DCC in a liquid form.

Step 3: Add molecular sieves at 10 g/100 ml of solution to absorb the water produced by the reaction and to pull the reaction equilibrium towards the formation of the product. Allow the reactants to mix at room temperature (no added heat) at least 6 hours or overnight. For a more rapid reaction rate, prepare a more concentrated reaction mixture. Step 4: The precipitate that forms is probably dicyclocarbohexylurea ("DCU"). Gravity filter the reaction mixture to remove the DCU crystals using Whatman 541 paper. Gravity filtration removes both the DCU crystals and the molecular sieves. Activated charcoal my optionally be added to remove any pigment that leaches off of the molecular sieves.

Step 5: Wash the crystals with THF.

Step 6: Rotary-evaporate the filtrate/product. Dry to crystals (triturated). Test the solubility of the crystals in a 1:1 mixture of chloroform and methanol. The crystals were insoluble in the above mixture. The crystals were fairly soluble in THF, and only marginally soluble in acetone.

Step 7: Perform thin layer chromatography ("TLC") on the reactants in acidic, basic and neutral solvent systems. The TLC plates are heat-activated, silica gel 60

TLC plates (E.M. Separations, Gibbstown, N.J.). Spray each plate with sterol-sensitive and ester-sensitive sprays. One new spot was found that was sterol- and ester-positive using the neutral TLC solvent system. TLC also showed that the basic system probably broke down the ester, due to the fact that there was an extra sterol-positive spot in the plate compared to the neutral system. In the acidic system (a mixture of chloroform: methanol: acetone: acetic acid: water, 50:10:20:10:5 (v/v)), everything except the NHS ran at the front. A mixture of toluene:acetonitril:acetic acid (100:20:1 by volume) was also run and a new spot was found just above the cholesterol reactant. Separation was minimal. The neutral system was the best of the 4 systems tested.

Step 8: The ester is purified by recrystallizing from 56° C. ethanol, using 100 ml ethanol per 0.5 g solid ester. Crystals are cooled overnight at −20° C. Wash crystals with ice-cold ethanol and recover by filtration. Perform TLC in chloroform: methanol: water at 65:24:4, (v/v). Purity should be greater than approximately 95%.

Reaction of Cholesterol-Ester and DMPE.

Briefly stated, the phosphatidylcholesterol is synthesized by reacting approximately 2 moles of Dimyristolylphosphatidylethanolamine ("DMPE"; 635.86 g/mol, with approximately one mole of the cholesterol ester prepared above (416 g/mole), with approximately 4 moles of triethylamine (101.19 g/mol). The reaction steps are as follows:

Step 1: Mix the cholesterol-ester prepared as described above (approximately 433 µmol) with 23 ml chloroform and with 2 ml tetrahydrofuran in a 125-ml round-bottom flask. Heat the mixture at 40° C. to completely dissolve the cholesterol-ester.

Step 2: Gradually add (5 ml at a time) 20 ml DMPE (Avanti Polar Lipids, Inc., Alabaster, Ala.; DMPE; 14:0), the DMPE being at a concentration of 20 mg/ml in chloroform (634 µmol).

Step 3: Add approximately 250 µL (1782 µmol) of triethylamine (J. T. Baker, Phillipsburg, N.J.) to the above mixture.

Step 4: Add a stir bar, purge the flask with nitrogen, and seal the flask with Parafilm.

Step 5: Place the reaction flask in a 600-ml flask half-filled with water with the heater set to 3, maintaining the temperature at 40° C. Set the stirrer to setting 4, and mix for six hours.

Step 6: Perform TLC on the reaction mixture using Cholesterol-ester, DMPE, and 5-Androsten-3β-OL-17β-carboxylic acid as standards. The same Rf pattern was found, i.e., a new, phosphate-positive/sterol-positive spot at Rf 0.8. Conversion appeared to be approximately 25%, based on the amount of ester and DMPE still present.

Step 7: Add an additional 0.5 ml triethylamine (3564 µmol), purge, seal, and mix at 40° C. for six hours. In steps 5 and 7 it is preferable to mix for approximately six hours as it decreases the possibility that triethylamine will convert the phospholipids (having two acyl chains each) to lyso-phospholipids (having one acyl chain each).

Step 8: A TLC of the products was performed in a mixture of chloroform: methanol: acetone: acetic acid: water, 50:10:20:10:5 (v/v), and showed that the ester was consumed. The products were Folch-extracted in 0.1N HC1, then 0.1N NaOH and then water. A TLC performed in the above mixture showed that the Folch removed most of the 5-Androsten-3β-OL-17β-carboxylic acid. The basic Folch probably deprotonated the COOH to COO—, thus increasing the hydrophilicity of the molecule. The basic Folch is probably all that is needed.

Step 9: Purification of the product is accomplished using high performance thin layer chromatography ("HPTLC") using 0.5 mm thick silica gel 60 TLC plates (E.M. Separations, Gibbstown, N.J.) having a preconcentration zone.

Step 10: TLC for column purification may be achieved by using chloroform neat, methanol neat, a 1:1 (v/v) mixture of chloroform and methanol, and a 2:8 ratio (v/v) mixture of chloroform and methanol. Preferably, the 1:1 (v/v) mixture of chloroform and methanol is used. There was some streaking in the 2:8 system and a little in the 1:1 system. Add 1% acetic acid to inhibit streaking. Used the above for the column. The acetic acid is probably not necessary. Rf in this system for the phosphatidylcholesterol (phosphate- and sterol-positive) was 0.94.

Step 11: Column purification: Dry sample and resuspend in 50:50:1 mixture of chloroform: methanol: acetic acid (v/v). De-gas the solvent with 25 mmHg on the vacuum pump. Load approximately 2 ml (est. 400 µmoles) of sample. Twenty minutes after loading, begin collecting 1 ml fractions. Collect 150 total fractions.

Step 12: TLC showed 3 phosphate- and sterol-positive compounds eluted. Fractions were assayed by phosphate, sterol, and ninhydrin stains. Spotted 5 µL of each fraction on TLC plate and then approximately 5 µL appropriate stain on top of each fraction spot. Results showed the first material eluted in fraction 65 (Pi and Sterol positive). Sterol started fading out at fraction 149. Ninhydrin started fading in at approximately fraction 146 (indicating free amine or DMPE beginning to elute). Actual running of fractions on TLC showed 3 groups of phosphate- and sterol-positive spots and ninhydrin-negative compounds. Rfs varied from approximately 0.95 to 0.85. This result could be due to protonation differences on amide or cholesterol ring systems. Collected three main fractions: 65→109; 110→120, and 121→141. Folch-extracted in water and added approximately ¹⁄₁₀th volume of 8% NaCl to force phase separation (via salt). The functions sat overnight in a cold room to separate.

Step 13: Recovered lower phases of each extract and re-extracted upper phases with approximately an equal volume of chloroform. Dried the lower phases on rotary evaporator and resuspended the residue in a 1:1 (v/v) mixture of chloroform and methanol. No acetic acid smell was present. TLC was performed in a 65:30:5 (v/v) mixture of chloroform:methanol:28% ammonium hydroxide, in a mixture of chloroform/methanol/water, and in a 50:50:1 (v/v) mixture of chloroform/methanol/acetic acid. Ran phosphate and cholesterol assays on each of the fractions: Fraction 1: pool of fractions 110>120 (pure by TLC); Fraction 2: pool of fractions 65→109 (not pure, two spots on TLC); Fraction 3: pool of fractions 121→141 (not pure, lower spot (Pi-+and Sterol-+and DMPE present on TLC).

Results

Fraction 1 (pool fcn 110–120): 5.05 mM, 6 ml=30 µmol total Pi.

Fraction 2 (pool fcn 65–109): 34.8 mM, 4 ml=140 µmol total Pi.

Fraction 3 (pool fcn 121–141): 20.2 mM, 3 ml=61 µmol total Pi.

The identity of the molecule is deduced by phosphate, iodine-, sterol, and ester-sensitive chemical sprays as well as the logic of reactivity of the intermediates. A final analysis by NMR is conducted to verify the structure of the analog.

Experiments using the above compound in liposomes have resulted in the generation of an IgG antibody that reacts with crystalline cholesterol, 43% cholesterol liposomes, and 71% liposomes. In the immune lysis assay (glucose release) the liposomes composed of 5% phosphatidylcholesterol (17β-Linkage) showed glucose release equivalent to liposomes containing 43% and 71% cholesterol. This broad reactivity of antisera raised by the compound may allow the production of a more sensitive ELISA as well as the production of a wider-spectrum anti-cholesterol vaccine.

EXAMPLE VII

Vaccine against Ergosterol

The ergosterol vaccine comprises as an active ingredient

A. a delivery vehicle and

B. either,
  (i) ergosterol; or
  (ii) ergosterol and an adjuvant; or
  (iii) ergosterol, phosphatidyl choline and an adjuvant; or
  (iv) ergosterol, dimyristoyl phosphatidyl choline and an adjuvant; or
  (v) ergosterol and phosphatidyl choline;
  (vi) ergosterol and dimyristoyl phosphatidyl choline; or
  (vii) dimyristoylphosphatidylglycerol.

It is to be understood that ergosterol derivatives may be used instead of ergosterol in the above vaccine compositions. Such ergosterol derivatives include, but are not limited to, phosphatidylergosterol.

EXAMPLE VIII

Immunization against ergosterol

Liposomes may be manufactured by standard methods in which liposomes loaded with ergosterol are prepared for injection as taught by Swartz et al. (Antibodies to cholesterol. Proc. Nat. Acad. Sci. 85:1902–1906, 1988 and Alving et al. (U.S. Pat. No. 4,885,256), both of which are incorporated by reference. The liposomes have relative molar ratio between ergosterol and lipid that is 1/13 of the above-described cholesterol liposomes. Thus, ergosterol-containing liposomes have ergosterol: lipid ratios of approximately 0.058:1 to approximately 0.69:1. A preferred ergosterol-containing liposome has an ergosterol: lipid ratio of 0.19:1. Liposomes may optionally contain lipid A as an adjuvant. Examples of other adjuvants that could be used in combination with lipid A or in place of lipid A include, but are not limited to, lipophilic muramyl dipeptide derivatives incorporated into liposomes, nonionic block polymers, and aluminum hydroxide or aluminum phosphate adjuvant.

EXAMPLE IX

Enzyme-Linked Immunosorbent Assay ("ELISA")

ELISAs are performed by using ergosterol as an antigen on the bottoms of the wells of microtiter plates. For example, ergosterol is coated onto the surface of wells in polystyrene plates (Immunlon 96, "U" bottom, Dynatech Laboratories, Alexandria, Va.) by addition of an ethanolic solution and evaporation of the solvent by air under a fume hood. Plates may be further dried under high vacuum and stored at −30° C. when not used the same day. Plates are blocked by any suitable blocking method known to one skilled in the art. For example, blocking may be performed by the addition of phosphate-buffered saline (PBS: 137 mM NaCl/2.7 mM KCl/9.6 mM phosphate, pH7.2) containing 10% heat-inactivated fetal bovine serum ("FBS") (M.A. Bioproducts, Walkersville, Md.). This is accomplished by washing the wells three times for 10 min each.

The detection of antibodies directed against ergosterol in body fluids of a mouse may be accomplished by adding to the coated wells fifty microliters of ascites fluid from a mouse, diluted in PBS containing 10% FBS, followed by incubation for 1 hr at room temperature. Plates are then washed three times for 5 minutes each with PBS. Fifty microliters of goat anti-mouse IgM (mu-chain) alkaline phosphatase conjugate (Kirkegaard and Perry Laboratories, Gaithersburg, Md.) at 1 microgram per ml in PBS containing 10% FBS is added to the wells and incubated 1 hour at room temperature. Plates again are washed three times for 5 minutes each PBS. Fifty microliters of the substrate, p-nitrophenyl phosphate at 2 mg/ml in diethanolamine buffer (Kirkegaard and Perry Laboratories) is added to the well and incubated 30 minutes at room temperature. Plates are then scanned for optical activity at 405 nm using a Titertek Multiscan (Flow Laboratories). Values are adjusted by subtracting the value in blank wells that lacked both antigen and monoclonal antibody. Optical activity shows that antibodies directed against ergosterol are present in the mouse, which therefore indicates that the mouse has been infected with the fungal infection. It is to be understood that an ELISA may be performed on body fluids such as ascites fluid from other animals, including humans.

EXAMPLE X

Ergosterol Immunization Protocol

An immunization protocol similar to that employed for cholesterol vaccine is used. Four groups of rabbits are either immunized with liposomes containing approximately 5 mol % ergosterol, or are not immunized. Immunization may be performed either intramuscularly or intravenously every two weeks for 6 weeks.

EXAMPLE XI

Fungal Challenge

At week 6, the animals are challenged with a fungal infection. Any of the common fungi would suffice for this purpose. Both the immunized and unimmunized animals subsequently are examined to determine whether and to what degree the fungal infection persists.

Mice are injected with a lethal fungal organism (e.g., aspergillosis or candidiasis and protection against death will be observed, as taught by Ahmad et al., Indian Journal of Biochemistry & Biophysics, Vol. 26, pp. 351–356., 1989, which is incorporated by reference.

Briefly, male BALB/C mice (body weight, 20–25 g) are injected with 0.17 µl of 0.15 m saline containing varying numbers of fungal spores. A spore dose of $1.8 \times 10^7$ aspergillus spores is sufficient to cause disseminated fungal infection. Different spore dosages may be required to elicit disseminated fungal infection for other fungi.

Mice are injected via the tail with the fungal spore dose. After 24 hours of spore challenge, the animals are randomly divided into groups of 15 animals each. One group receives liposome free treatments, another receives liposomes only, one group receives sterol-containing liposomes, and a final group receives no treatment at all. Efficacy of treatment is evaluated on the basis of survival and colony forming units ("CFU") in the lungs. CFU is determined by sacrificing an animal and removing the left lung aseptically. The lung is homogenized, and serial dilutions are plated on nutrient plates. After 24 hours incubation colonies are counted.

EXAMPLE XII

Brief Summary of the Synthesis of N-[(3β,22E)-Ergosta-5, 7,22-Trien-3-(Succinylamido)] Dimyristoylphosphatidylethanolamine: The trivial Name of which is Phosphatidylergosterol The synthesis of a molecule that increases the exposure of the ergosterol ring system in liposomal bilayers to improve the immunogenicity of ergosterol for the production of a vaccine is described in this example. Briefly summarized, phosphatidylergosterol is synthesized by reacting an N-hydroxysuccinimide ester of ergosterol hemisuccinate with dimyristoylphosphatidyl-ethanolamine ("DMPE"). DMPE is selected to provide the primary amino group that reacts with the N-hydroxysuccinimide ester and because its acyl chains are identical to those of the lipids DMPC and DMPG that are used in the vaccines of the present invention. The synthesis starts with ergosterol and ends with the phosphatidylergosterol.

All manipulations take place under low light conditions.

Step I Synthesis of Ergosterol Hemisuccinate

1. In a 25×150 mm glass tube with a Teflon-lined screw cap, dissolve 2 grams (5 mmol) recrystallized ergosterol (See Example XIII) and 5 grams (50 mmol) succinic anhydride (J. T. Baker, Phillipsburg, N.J.) in 12 ml anhydrous pyridine. Add a stir bar, purge the tube with argon, and seal and cover the tube with aluminum foil.
2. Mix at room temperature for 4 days.
3. Add 1.5 ml cold deionized water and mix for 1 hour.
4. Extract the mixture with ethyl acetate. Recover the organic layer.
5. Wash the organic layer with water. Recover the organic layer.
6. Dry the organic layer by rotary evaporation. A brown residue remains.
7. Add 50 ml methanol to the organic residue to remove pyridine. Repeat.
8. For large amounts of residue, purify the residue using BioSil A ("Bio-Rad") Silicic acid eluted with a 16:1 mixture of chloroform:methanol (v/v). Collect 2-ml fractions. Pool fractions 26–61. To purify small amounts of the residue, use high performance thin layer chromatography ("HPTLC") using 0.5 mm thick silica gel 60 TLC plates (E.M. Separations, Gibbstown, N.J.), having a preconcentration zone.
9. Assess conversion by thin-layer chromatography using heat-activated, silica gel 60 TLC plates (E.M. Separations, Gibbstown, N.J.) eluted with a mixture of chloroform:hexane:diethyl ether:acetic acid, 10:9:1:0.1 (v/v) and visualized with iodine vapor. A new spot appeared on the TLC plate (Rf 0.17) that did not run with ergosterol (Rf 0.22) or any of the reactants. Purity was estimated to be approximately 80% by TLC. Performed a spectrophotometric scan from 300–260 nm. The spectrum of the new product strongly resembled that of ergosterol. The new compound also reacted positively with sterol-sensitive chemical spray. The calculated molecular weight of the product is 497.

Step II: Formation of Ergosterol-N-Hydroxy-Succinimide Ester from Ergosterol Hemisuccinate.

1. In a 25-ml glass Erlenmeyer flask dissolve 856 mg (1.7 mmol) of the ergosterol hemisuccinate formed in Step 1, and 196 mg (1.7 mmol) N-hydroxysuccinimide ("NHS"; Aldrich, Milwaukee, Wis.) in 5 ml anhydrous tetrahydrofuran.
2. Melt solid dicyclohexylcarbodiimide ("DCC": the catalyst) in a 45° C. water bath and pipet 281 μL (1.7 mmol, at a concentration of 1.247 g/ml) into the reaction mixture.
3. Add 0.5 g of molecular sieves to remove water formed in the reaction, and to pull the reaction equilibrium towards formation of the ester.
4. Purge the flask with argon, add a stir bar, seal and cover with foil, and mix 6 hours at room temperature.
5. Filter off sieves and collect filtrate.
6. Dry filtrate under argon stream. Resuspend the filtrate in chloroform.
7. TLC in a mixture of chloroform:methanol:water, 65:25:4 (v/v). A new compound at Rf 0.99 was found. This compound reacted positively with ester-sensitive spray on TLC. Yield was 77% (1.313 mmols; 780 mg). Ergosterol hemisuccinate ran at Rf 0.95.

Step III: Condensation of Ergosterol-N-Hydroxysuccinimide Ester ("Erg-NHS-Ester") with DMPE.

1. Dry filtrate from above and resuspend in approximately 30 ml dry tetrahydrofuran, 46 mg (0.077 mmol) ERG-NHS-Ester and 32.6 mg (0.0513 mmol) DMPE.
2. Add 129 μL (0.924 mmol) triethylamine. Purge with argon and seal.
3. Mix for six hours.
4. Dry the reaction under a stream of argon.
5. Folch extract with total volume of 68 ml of a mixture of chloroform:methanol:0.1 N HCL, 2:2:1.8 (v/v). A yellow-brown lower phase is recovered. Reextract the upper phase.
6. Dry the lower phases on a rotary evaporator, and vacuum desiccate overnight.
7. Perform TLC in a mixture of chloroform: methanol:acetone:acetic acid:water, 50:10:20:10:5 (v/v). Results showed a new, phosphate-positive/sterol-positive spot (Rf 0.91) that did not run with any of the reactants.
8. Purification of the product is accomplished using high performance thin layer chromatography ("HPTLC") using 0.5 mm thick silica gel 60 TLC plates (E.M. Separations, Gibbstown, N.J.) having a preconcentration zone.

The identity of the resulting compound is deduced by phosphate-, sterol-, ester- and iodine-sensitive chemical reagents. NMR analysis is conducted to verify the structure of the compound.

EXAMPLE XIII

Recrystallization of Ergosterol.

As ergosterol from Aldrich is manufactured in batches of varying purity, and it is converted to an undesirable byproduct upon exposure to light, it must be recrystallized prior to its use in the synthesis of phosphatidylergosterol. Briefly, ergosterol is purified by its recrystallization from ethyl acetate, and then by its recrystallization from dichloroethane. Although any method known in the art may be used to recrystallize ergosterol, the following method is preferred:

First Crystallization

1. All procedures are carried out under low-light conditions. Place 2 grams of ergosterol (Aldrich, Milwaukee, Wis.) into a clean, dry 250-ml Erlenmeyer flask.
2. Add 50 mL of room temperature ethyl acetate and seal the flask. Ergosterol is not soluble.
3. Heat the mixture to 50° C. with swirling until the ergosterol dissolves (about 10 minutes).

4. Place the flask at −20° C. for 45 minutes. White crystals will appear.
5. Filter the crystals and wash thoroughly with ice-cold ethyl acetate to remove any remaining yellow contaminants. Filter with Whatman 541 filter paper with a Standard Buchner funnel and a vacuum collar.
6. Desiccate the crystals for approximately two to three days in the dark.
7. At least approximately 915 mg solid will be recovered.

Second Crystallization

1. Place 915 mg of once-recrystallized ergosterol (from the above first step) into a 25-ml Erlenmeyer flask.
2. Add 15 ml dichloroethane to the flask and seal the flask.
3. Heat the mixture to 65° C. with constant swirling until the crystals dissolve (about 10 minutes).
4. Cover the flask with aluminum foil and place in fume hood for approximately 1 hour.
5. Place the flask at 4° C. overnight.
6. Wash the crystals with cold dichloroethane.
7. Desiccate the crystals overnight to produce white, fluffy, chloroform soluble crystals.
8. Protect the crystals from light by wrapping them in foil, and store the crystals under nitrogen or argon. Routine use of the ergosterol crystals will decrease its purity through repeated exposure to light. Therefore, the compound is to be stored in the dark.

It should be understood, of course, that the foregoing relates only to a preferred embodiment of the present invention and that numerous modifications or alterations may be made therein without departing from the spirit and the scope of the invention as set forth in the appended claims.

We claim:

1. A vaccine comprising a liposome comprising between about 55.5 mol % and 71 mol % cholesterol, and either phosphatidyl choline or dimyristoyl phosphatidyl choline, for immunizing or hyperimmunizing a mammal against cholesterol.

2. The vaccine of claim 1, wherein the liposome contains phosphatidyl choline.

3. The vaccine of claim 1, wherein the liposome contains dimyristoyl phosphatidyl choline.

4. The vaccine of claim 1, further comprising an adjuvant.

5. The vaccine of claim 4, wherein the adjuvant is selected from the group consisting of lipophilic muramyl dipeptide derivatives, nonionic block polymers, aluminum hydroxide, aluminum phosphate, and lipid A.

6. The vaccine of claim 5, wherein the adjuvant is lipid A.

7. A therapeutic method for vaccinating a mammal against cholesterol to treat or prevent hypercholesterolemia or atherosclerosis comprising, administering to the mammal an amount effective to immunize the mammal against cholesterol of a vaccine comprising a liposome comprising between about 43 mol % and 71 mol % cholesterol, and either phosphatidyl choline or dimyristoyl phosphatidyl choline.

8. The method of claim 7, wherein the liposome contains phosphatidyl choline.

9. The method of claim 7, wherein the liposome contains dimyristoyl phosphatidyl choline.

10. The method of claim 7, wherein the vaccine further comprises an adjuvant.

11. The method of claim 10, wherein the adjuvant is selected from the group consisting of lipophilic muramyl dipeptide derivatives, nonionic block polymers, aluminum hydroxide, aluminum phosphate, and lipid A.

12. The method of claim 11, wherein the adjuvant is lipid A.

13. The vaccine of claim 1, wherein the mammal is a human.

14. The vaccine of claim 1, wherein the liposome comprises greater than 60 mol % cholesterol.

15. The vaccine of claim 1, wherein the liposome comprises approximately 71 mol % cholesterol.

16. The method of claim 7, wherein the mammal is a human.

17. The method of claim 7, wherein the liposome comprises greater than 50 mol % cholesterol.

18. The method of claim 7, wherein the liposome comprises greater than 60 mol % cholesterol.

19. The method of claim 7, wherein the liposome comprises approximately 71 mol % cholesterol.

* * * * *